United States Patent
Ilekti et al.

(10) Patent No.: US 10,485,743 B2
(45) Date of Patent: *Nov. 26, 2019

(54) COSMETIC COMPOSITION FOR COATING KERATIN FIBRES

(71) Applicant: L'OREAL, Paris (FR)

(72) Inventors: Philippe Ilekti, Maisons-Alfort (FR); Nathalie Jager Lezer, Verrieres-le-Buisson (FR)

(73) Assignee: L'OREAL, Paris (FR)

( * ) Notice: Subject to any disclaimer, the term of this patent is extended or adjusted under 35 U.S.C. 154(b) by 304 days.

This patent is subject to a terminal disclaimer.

(21) Appl. No.: 15/028,289

(22) PCT Filed: Sep. 23, 2014

(86) PCT No.: PCT/FR2014/052369
§ 371 (c)(1),
(2) Date: Apr. 8, 2016

(87) PCT Pub. No.: WO2015/052399
PCT Pub. Date: Apr. 16, 2015

(65) Prior Publication Data
US 2016/0262996 A1    Sep. 15, 2016

(30) Foreign Application Priority Data

Oct. 11, 2013 (FR) ...................... 13 59890

(51) Int. Cl.
| | | |
|---|---|---|
| *A61Q 1/10* | (2006.01) | |
| *A61K 8/33* | (2006.01) | |
| *A61K 8/25* | (2006.01) | |
| *A61K 8/39* | (2006.01) | |
| *A61K 8/49* | (2006.01) | |
| *A61K 8/60* | (2006.01) | |
| *A61K 8/86* | (2006.01) | |
| *A61K 8/02* | (2006.01) | |
| *A61K 8/04* | (2006.01) | |
| *A61K 8/19* | (2006.01) | |
| *A61K 8/37* | (2006.01) | |
| *A61K 8/55* | (2006.01) | |
| *A61K 8/895* | (2006.01) | |
| *A61K 8/92* | (2006.01) | |

(52) U.S. Cl.
CPC ............... *A61K 8/33* (2013.01); *A61K 8/025* (2013.01); *A61K 8/0295* (2013.01); *A61K 8/04* (2013.01); *A61K 8/19* (2013.01); *A61K 8/25* (2013.01); *A61K 8/37* (2013.01); *A61K 8/375* (2013.01); *A61K 8/39* (2013.01); *A61K 8/4993* (2013.01); *A61K 8/55* (2013.01); *A61K 8/60* (2013.01); *A61K 8/86* (2013.01); *A61K 8/895* (2013.01); *A61K 8/92* (2013.01); *A61Q 1/10* (2013.01); *A61K 2800/52* (2013.01); *A61K 2800/596* (2013.01)

(58) Field of Classification Search
None
See application file for complete search history.

(56) References Cited

U.S. PATENT DOCUMENTS

| | | | | |
|---|---|---|---|---|
| 6,517,823 | B1 * | 2/2003 | Norman | .................... A61K 8/39 |
| | | | | 424/400 |
| 2009/0016982 | A1 | 1/2009 | Raineau | |
| 2009/0142289 | A1 * | 6/2009 | Arditty | .................. A61K 8/922 |
| | | | | 424/70.7 |
| 2010/0310486 | A1 * | 12/2010 | Blin | ....................... A61K 8/0229 |
| | | | | 424/64 |
| 2011/0243869 | A1 * | 10/2011 | Brijlall | ..................... A61K 8/25 |
| | | | | 424/70.6 |

FOREIGN PATENT DOCUMENTS

| | | | |
|---|---|---|---|
| JP | 2008-120817 | A | 5/2008 |
| JP | 2008-179647 | A | 8/2008 |
| JP | 2009-46485 | A | 3/2009 |
| JP | 2011-503141 | A | 1/2011 |
| WO | WO 2014/060309 | A1 | 4/2014 |

OTHER PUBLICATIONS

International Search Report dated Dec. 19, 2014, in PCT/FR2014/052369 filed Sep. 23, 2014.

* cited by examiner

*Primary Examiner* — Jyothsna A Venkat
(74) *Attorney, Agent, or Firm* — Oblon, McClelland, Maier & Neustadt, L.L.P.

(57) ABSTRACT

The present invention relates to a cosmetic composition for coating keratin fibers, comprising:
  an aqueous phase,
  a surfactant system present at a total content of greater than or equal to 15% by weight relative to the total weight of the composition, said surfactant system comprising:
    i) at least one nonionic surfactant with an HLB value at 25° C. of less than 8, and
    ii) at least one nonionic surfactant with an HLB value at 25° C. of greater than or equal to 8, together forming a lamellar phase Lβ, and
  at least one spherical filler.
The present invention also relates to a process for coating keratin fibers.

20 Claims, No Drawings

COSMETIC COMPOSITION FOR COATING KERATIN FIBRES

The present invention relates to a cosmetic composition for coating keratin fibres, and in particular the eyelashes or the eyebrows. In particular, said cosmetic composition is a composition for making up and optionally caring for the eyelashes. The present invention also relates to a process for coating keratin fibres, in particular a process for making up and optionally caring for the eyelashes. The present invention also relates to particular uses.

The composition used may in particular be in the form of an eyelash product such as a mascara, or an eyebrow product. More preferentially, the invention relates to a mascara. The term "mascara" means a composition intended to be applied to the eyelashes: it may be an eyelash makeup composition, an eyelash makeup base (also known as a base coat), a composition to be applied over a mascara, also known as a top coat, or else a cosmetic composition for treating the eyelashes. The mascara is more particularly intended for human eyelashes, but also for false eyelashes.

Mascaras conventionally comprise a not insignificant amount of waxes and are commonly prepared according to two types of formulation: water-based mascaras known as cream mascaras, in the form of a dispersion of waxes in water; anhydrous mascaras or mascaras with a low water content, known as waterproof mascaras, in the form of dispersions of waxes in organic solvents.

Generally, anhydrous mascaras have good water resistance, but the volume level is generally low and they are difficult to remove, whereas water-based mascaras have lower water resistance but a high volume level and are easier to remove.

The present patent application more specifically relates to "water-based" mascaras.

The application of mascara is in particular directed towards increasing the volume of the eyelashes and consequently increasing the intensity of the gaze. Numerous thickening or volumizing mascaras exist to do this, the principle of which consists in depositing a maximum amount of material onto the eyelashes so as to obtain this volumizing (or charging) effect. It is in particular by means of the amount of particles (in particular waxes) that the desired application specificities for the compositions may be adjusted, for instance their fluidity or consistency, and also their thickening power (also known as the charging or makeup power).

However, in order to succeed in depositing a thick deposit on the eyelash, the mascara composition must have a high concentration of ingredient. However, it turns out that a conventional mascara composition comprising waxes in high concentration may occasionally be unpleasant on application since it is occasionally too solid and thus no more applicable.

This problem is in particular encountered with the conventional formulation routes for water-based mascaras which do not allow a high solids content, for example greater than or equal to 42%, to be exceeded, otherwise the texture is too thick.

Application EP 1 920 759 proposes structuring mascara compositions using waxes, in order to obtain a thick texture and a volumizing deposit. In order to homogeneously disperse these waxes, a system of specific surfactants must be used, comprising an alkyl phosphate and an ether of fatty alcohol and of polyethylene glycol having an HLB of strictly less than 8. Said application illustrates several examples of mascara compositions comprising 20.14% by weight of waxes, for at most 10% by total weight of surfactants, relative to the total weight of the composition, with the surfactants essentially acting as an emulsifier for these waxes.

Application FR 2 960 151, for its part, proposes promoting the persistence and the resistance to crumbling by using a specific surfactant system comprising an alkyl phosphate and an ether of fatty alcohol and of polyethylene glycol having an HLB of strictly less than 8, combined with a specific waxy phase. Said application illustrates several examples of mascara compositions comprising more than 25.59% by weight of waxes, emulsified by means of the abovementioned surfactant system.

An aim of the present invention is thus to obtain a novel formulation route for a mascara which is pleasant to apply and whose volume builds up gradually in the course of applications.

An aim of the present invention is more particularly to provide a mascara preferably with a high solids content, for example greater than or equal to 42%.

More particularly, an aim of the present invention consists in stabilizing a mascara without phase separation over time and/or with respect to UV radiation and/or with respect to light.

An aim of the present patent application is more particularly to provide a stable mascara, which has a texture that is thick enough to obtain a charging deposit, of satisfactory consistency, allowing easy application to the eyelashes and an even deposit, i.e. a deposit which is smooth and uniform.

An aim of the present patent application is more particularly to provide a mascara in which the pigments are uniformly dispersed.

An aim of the present patent application is more particularly to provide a mascara that is pleasant upon application.

An aim of the present invention is more particularly to propose a composition for coating keratin fibres that allows good separation of the eyelashes when applied, without forming bundles of eyelashes, and doing so while ensuring a smooth and uniform deposition of material (no lumps of composition).

An aim of the present invention is more particularly to obtain a composition for coating keratin fibres, preferably a mascara, which has good application properties in terms of glidance and play time (redeposition, retouching).

An aim of the present invention is also to obtain a composition for coating keratin fibres, preferably a mascara, which produces a volumizing effect on the eyelashes, this preferably being despite the presence of a low amount of waxes, or even this being despite the absence of waxes.

An aim of the present invention is also to obtain a composition for coating keratin fibres, preferably a mascara, which has good persistence on the eyelashes.

An aim of the present invention is also to obtain a composition for coating keratin fibres, preferably a mascara, which produces a charging or covering deposit.

An aim of the present invention is also to obtain a composition for coating keratin fibres, preferably a mascara, which has good lengthening properties for eyelashes coated with such a composition.

An aim of the present invention is also to obtain a composition for coating keratin fibres, preferably a mascara, which has good curling properties for eyelashes coated with such a composition.

An aim of the present invention is also to obtain a composition for coating keratin fibres, preferably a mascara, which has good adhesion to the eyelashes.

Consequently, a subject of the present invention is a cosmetic composition for coating keratin fibres, preferably the eyelashes, preferably a mascara composition of the continuous aqueous phase type, comprising:
- an aqueous phase,
- a surfactant system present at a total content of greater than or equal to 15% by weight relative to the total weight of the composition, said surfactant system comprising, preferably essentially constituted of, or even constituted of:
  - i) at least one nonionic surfactant with an HLB value at 25° C. of less than 8, and
  - ii) at least one nonionic surfactant with an HLB value at 25° C. of greater than or equal to 8, together forming a lamellar phase Lβ, and
- at least one spherical filler.

Surprisingly and unexpectedly, the inventors of the present patent application have solved this (these) problem(s) by means of such a composition. In particular, a composition in accordance with the invention gives rise to a composition which may be rich in solids, especially in particles such as in filler(s) and/or pigment(s), which has a homogeneous and uniform dispersion of particles, which is pleasant to apply, comfortable, and which has a volumizing effect.

According to the inventors, a paracrystalline lamellar phase Lβ as described above allows an excellent compromise between texture and cosmeticity and confers a charging effect while dispensing with wax(es) which are nevertheless conventionally used in mascara to obtain a good charging effect. This new formulation route thus makes it possible, surprisingly, to dispense with the use of waxes, which are nevertheless conventional in a mascara.

A system in accordance with the invention may optionally essentially consist of, or even may consist of:
- i) at least one nonionic surfactant with an HLB value at 25° C. of less than 8, and
- ii) at least one nonionic surfactant with an HLB value at 25° C. of greater than or equal to 8, together forming a lamellar phase Lβ.

According to a second aspect, a subject of the present invention is also an assembly or kit for coating keratin fibres, comprising:
- at least one cosmetic composition for coating keratin fibres as described previously, and
- at least one applicator for the composition, said applicator comprising means, where appropriate with reliefs, configured to come into contact with said keratin fibres, such as the eyelashes or the eyebrows, so as to smooth and/or separate the eyelashes or the eyebrows. Such reliefs may comprise teeth, bristles or the like. Said assembly, and in particular said applicator, may optionally be equipped with means for vibrating and/or heating said composition.

According to a third aspect, a subject of the present invention is also an assembly or kit for packaging and applying a composition for coating keratin fibres, comprising:
- a device for packaging said cosmetic composition for coating keratin fibres as described previously,
- an applicator for said composition.

Said applicator may be integrally attached to a gripping member forming a cap for said packaging device. In other words, said applicator may be mounted in a removable position on said device between a closed position and an open position of a dispensing aperture of the device for conditioning said composition.

According to a fourth aspect, a subject of the present invention is also a process for coating keratin fibres, in particular for making up the eyelashes, comprising a step of applying a cosmetic coating composition as defined previously.

According to particular preferred embodiments of the present invention concerning both the compositions and the processes described above and directed towards solving at least one of the abovementioned problems:
- the aqueous phase represents from 30% to 70% by weight and preferably from 40% to 60% by weight relative to the total weight of the composition;
- the composition has a continuous aqueous phase;
- the nonionic surfactant(s) with an HLB value at 25° C. of greater than or equal to 8 preferably have an HLB value at 25° C. of greater than or equal to 10;
- the at least one from among the nonionic surfactant(s) with an HLB value at 25° C. of less than 8 is chosen from:
  - esters and ethers of monosaccharides which are optionally (poly)oxyalkylenated, preferably (poly)oxyalkylenated;
  - esters of fatty acids, in particular of $C_8$-$C_{24}$ and preferably of $C_{16}$-$C_{22}$ fatty acids, and of polyol, which is optionally (poly)oxyalkylenated, preferably (poly)oxyalkylenated, in particular of (poly)oxyalkylenated glycerol or of oxyalkylenated sorbitol, preferably of (poly)oxyalkylenated glycerol;
  - alcohols which are optionally (poly)oxyalkylenated, preferably (poly)oxyalkylenated;
  - and mixtures thereof; preferably from among alcohols which are optionally (poly)oxyalkylenated, preferably (poly)oxyalkylenated;
- the at least one from among the nonionic surfactant(s) with an HLB value at 25° C. of less than 8 comprises an alcohol which is optionally (poly)oxyalkylenated, preferably (poly)oxyalkylenated, comprising an ether of a $C_8$-$C_{24}$ fatty alcohol and of polyethylene glycol, said ether comprising from 1 to 10 and better still between 2 and 6 ethylene glycol units;
- the nonionic surfactant(s) with an HLB value at 25° C. of greater than or equal to 8, preferably greater than or equal to 10, are chosen from:
  - (poly)oxyalkylenated glycerol ethers,
  - (poly)oxyalkylenated alcohols,
  - fatty acid esters of (poly)oxyalkylenated polyethylene glycol,
  - fatty acid esters of (poly)oxyalkylenated glyceryl ethers,
  - fatty acid esters of (poly)oxyalkylenated sorbitol ethers,
  - and mixtures thereof; preferably from (poly)oxyalkylenated alcohols;
- the at least one from among nonionic surfactants with an HLB value at 25° C. of greater than or equal to 8 comprises a (poly)oxyalkylenated alcohol comprising at least one $C_8$-$C_{24}$ fatty alcohol ether of polyethylene glycol, said ether comprising more than 10 ethylene glycol units, better still between 15 and 200 ethylene glycol units;
- the nonionic surfactant(s) with an HLB value at 25° C. of less than 8, preferably corresponding to formula (I), are present in a content of greater than or equal to 5% by weight relative to the total weight of the composition, preferably between 7% and 30%, preferably between 10% and 20% by weight relative to the total weight of the composition;
- the nonionic surfactant(s) with an HLB value at 25° C. of greater than or equal to 8, preferably greater than or equal to 10, preferably corresponding to formula (I), are present in a content of greater than or equal to 5% by weight relative to the total weight of the composition, preferably between 7% and 30%, preferably between 10% and 20% by weight relative to the total weight of the composition;

the nonionic surfactant(s) with an HLB value at 25° C. of less than 8 and the nonionic surfactant(s) with an HLB value at 25° C. of greater than or equal to 8, both preferably corresponding to formula (I), are present in a total content of greater than or equal to 15%, in particular between 16% and 40%, preferably between 18% and 30% by weight, relative to the total weight of the composition;

the nonionic surfactant(s) with an HLB value at 25° C. of less than 8 and the nonionic surfactant(s) with an HLB value at 25° C. of greater than or equal to 8, both preferably corresponding to formula (I), are present in a respective total content such that the weight ratio of the nonionic surfactant(s) with an HLB value at 25° C. of less than 8 to the nonionic surfactant(s) with an HLB value at 25° C. of greater than or equal to 8, ranges from 1/5 to 5, preferably from 1/3 to 3, preferably from 2/3 to 3/2;

the spherical filler(s) are preferably chosen from:
  silica powders;
  powders of acrylic (co)polymers, and derivatives thereof, in particular powders of acrylate (co)polymer, and derivatives thereof;
  polyurethane powders;
  silicone powders;
  polyamide powders;
and a mixture or mixtures thereof, preferably from powders of acrylic (co)polymers, and derivatives thereof, in particular powders of acrylate (co)polymer, polyurethane powders, and a mixture or mixtures thereof;

the spherical filler(s) are present in a total content of greater than or equal to 5% by weight, relative to the total weight of the composition, for example between 8% and 30% by weight, preferably between 8% and 25% by weight, better still between 10% and 20% by weight, relative to the total weight of the composition;

the composition comprises at least one lamellar filler;

the lamellar filler(s) are chosen from talc, natural or synthetic mica, certain silicas, clays such as magnesium aluminium silicates, trimethyl siloxysilicate, kaolin, bentone, calcium carbonate and magnesium hydrogen carbonate, hydroxyapatite, boron nitride, fluorphlogopite, perlite powders, an N-lauroyl lysine powder, and a mixture or mixtures thereof;

the lamellar filler(s) are chosen from talc, mica, fluorphlogopite, clays such as magnesium aluminium silicate, an N-lauroyl lysine powder, and a mixture or mixtures thereof;

the lamellar filler(s) are present in a total content of greater than or equal to 5% by weight, relative to the total weight of the composition, for example between 8% and 30% by weight, preferably between 8% and 25% by weight, better still between 10% and 20% by weight, relative to the total weight of the composition;

the composition comprises a content of wax(es) strictly less than 10% by weight relative to the total weight of the composition, preferably less than or equal to 5% by weight, better still less than or equal to 2% by weight, or even is free of wax(es);

the total content of spherical filler(s) and the total content of surfactant system are such that the weight ratio of the spherical filler(s)/the surfactant system is greater than 1/10, preferably between 1/5 and 6/5;

said composition is free of oil or organic solvent;

said composition comprises a solids content of greater than or equal to 42%, preferentially greater than or equal to 45%, more preferentially greater than or equal to 48%, or even greater than or equal to 50% and advantageously less than 60%;

said composition comprises particles of film-forming polymer(s) present in aqueous dispersion form for example according to a content of greater than or equal to 5% by weight, preferably greater than or equal to 10% by weight, more preferentially between 10% and 30% by weight, relative to the total weight of the composition;

the particles of film-forming polymer(s) present in aqueous dispersion form are chosen from synthetic polymers, of radical type or of polycondensate type, polymers of natural origin, and mixtures thereof;

the particles of film-forming polymer(s) present in aqueous dispersion form are chosen from acrylic polymer dispersions, polyurethane dispersions, sulfopolyester dispersions, vinyl dispersions, polyvinyl acetate dispersions, vinylpyrrolidone, dimethylaminopropylmethacrylamide and lauryldimethylpropylmethacrylamidoammonium chloride terpolymer dispersions, dispersions of polyurethane/polyacrylic hybrid polymers, dispersions of particles of core-shell type and mixtures thereof, preferably from acrylic polymer dispersions, dispersions of polyurethane/polyacrylic hybrid polymers, and derivatives thereof, and a mixture or mixtures thereof, preferentially from acrylic in particular styrene-acrylic, polymer dispersions, and polyurethane, in particular polyester-polyurethane, dispersions, and derivatives thereof, and a mixture or mixtures thereof;

said composition comprises at least one water-soluble film-forming polymer, more preferentially said composition is free of water-soluble film-forming polymer;

said composition comprises at least one dye chosen from one or more pulverulent substance(s), preferably metal oxides, and in particular iron oxides;

the metal oxide(s) are preferably present in a content of greater than or equal to 5% by weight relative to the total weight of the composition, and advantageously inclusively between 6% and 22% by weight relative to the total weight of the composition;

said composition comprises at least one hydrophilic and/or lipophilic gelling agent, preferably at least one hydrophilic gelling agent;

said composition has a viscosity at 25° C. ranging from 5 to 50 Pa·s, in particular measured using a Rheomat RM100® machine;

said composition may be a makeup composition, a makeup base or "base coat", or a "top coat" composition to be applied onto a makeup.

Other characteristics, properties and advantages of the present invention will emerge more clearly on reading the description and the examples that follow.

Aqueous Phase

The composition according to the invention comprises an aqueous phase, which advantageously forms a continuous phase of the composition.

The term "composition with an aqueous continuous phase" means that the composition has a conductivity, measured at 25° C., of greater than or equal to 23 ρS/cm (microSiemens/cm), the conductivity being measured, for example, using an MPC227 conductimeter from Mettler Toledo and an Inlab730 conductivity measuring cell. The measuring cell is immersed in the composition so as to remove the air bubbles that might be formed between the two electrodes of the cell. The conductivity reading is taken once the conductimeter value has stabilized. A mean is determined on at least three successive measurements.

The aqueous phase comprises water. It may also comprise at least one water-soluble solvent.

In the present invention, the term "water-soluble solvent" denotes a compound that is liquid at ambient temperature and water-miscible.

The water-soluble solvents that may be used in the compositions according to the invention may also be volatile.

Among the water-soluble solvents that may be used in the compositions in accordance with the invention, mention may be made in particular of lower monoalcohols containing from 1 to 5 carbon atoms such as ethanol and isopropanol, and glycols containing from 2 to 8 carbon atoms such as ethylene glycol, propylene glycol, 1,3-butylene glycol and dipropylene glycol.

The aqueous phase (water and optionally the water-miscible solvent) is generally present in the composition according to the present patent application in a content ranging from 30% to 70% by weight relative to the total weight of the composition, and preferably ranging from 40% to 60% by weight relative to the total weight of the composition. This aqueous phase content includes not only the water originating from the aqueous dispersions of film-forming polymers, and, where appropriate, from the aqueous dispersions of hard waxes, in accordance with the invention, but also, where appropriate, the water deliberately added to the composition.

Solids Content

The composition according to the invention advantageously comprises a solids content of greater than or equal to 42%, in particular greater than or equal to 45%, or even greater than or equal to 48% and preferentially greater than or equal to 50%, and advantageously less than 60%.

For the purposes of the present invention, the "solids content" denotes the content of non-volatile matter.

The solids content (abbreviated as SC) of a composition according to the invention is measured using a Halogen Moisture Analyzer HR 73 commercial halogen desiccator from Mettler Toledo. The measurement is performed on the basis of the weight loss of a sample dried by halogen heating, and thus represents the percentage of residual matter once the water and the volatile matter have evaporated off.

This technique is fully described in the machine documentation supplied by Mettler Toledo.

The measuring protocol is as follows:

Approximately 2 g of the composition, referred to hereinbelow as the sample, are spread out on a metal crucible, which is placed in the halogen desiccator mentioned above. The sample is then subjected to a temperature of 120° C. until a constant weight is obtained. The wet mass of the sample, corresponding to its initial mass, and the dry mass of the sample, corresponding to its mass after halogen heating, are measured using a precision balance.

The experimental error associated with the measurement is of the order of plus or minus 2%.

The solids content is calculated in the following manner:

Solids content(expressed as weight percentage)=
100×(dry mass/wet mass).

A composition according to the invention comprises wax particles, film-forming polymer particles and at least one particular surfactant system.

Lamellar Phase Lβ

Thus, a subject of the present patent application is a composition containing, in an aqueous medium, a surfactant system organised in the form of a lamellar phase Lβ, or paracrystalline phase Lβ, or lamellar gel phase.

This composition is stable at ambient temperature of 25° C. with a viscosity preferentially ranging from 5 to 50 Pa·s, measured at a ambient temperature of 25° C. using a Rheomat RM 100® rheometer.

The term "lamellar gel phase" or "paracrystalline phase Lβ" means a phase in which the surfactant molecules and/or more generally the molecules of amphiphilic compounds are organized in the form of bimolecular layers spaced apart by aqueous leaflets. Within the bimolecular layers, the molecules are distributed in a hexagonal geometry, their hydrocarbon-based chains are in a crystalline state and are oriented perpendicular to the plane of the bimolecular layers but have no specific orientation relative to each other in the plane of these layers.

The paracrystalline phases Lβ are metastable phases in which the fatty chains are in solid form and are arranged randomly relative to each other, unlike the micellar, hexagonal, cubic and lamellar fluid paracrystalline phases (Lα) in which the fatty chains are in liquid form, and unlike the crystalline phases in which the fatty chains are in solid form and oriented in an ordered manner relative to each other. The Applicant has found a particular surfactant system that makes it possible to obtain a stable paracrystalline phase Lβ, and thus cosmetic compositions for coating keratin fibres, in particular the eyelashes, which are stable and pleasant upon application using a particular system of a type of surfactants in particular contents.

To identify the lamellar gel phase or paracrystalline phase Lβ of the surfactant system present in the composition of the invention, use may be made of various techniques, and in particular the technique of wide-angle X-ray scattering.

Wide Angle X-Ray Scattering—WAXS

X-ray diagrams were recorded by a Mar345 image plate detector (Maresearch, Norderstedt, Germany), mounted on a FR591 rotary anode X-ray generator (Brüker, Courtaboeuf, France), used at 50 kV and at 50 mA. The monochromatic CuKα radiation ($\lambda$=1,541 Å) was focused with a 350 μm focal spot at 320 mm by double reflection on an elliptic cross-section multilayer Montel mirror (Incoatec, Geesthacht, Germany). The beam was defined under vacuum by four motorized carbon-tungsten slits (JJ-Xray, Roskilde, Denmark) positioned in front of the mirror (500 μm). Four additional guard slits were placed at the focal point with a 220 mm slit separation. The flux after the output mica windows was $3\times10^8$ photons/s. A 2-mm diameter circular metal wire beam stop was placed in air at 150 mm after the sample, and the detector was positioned at 360 mm. The X-ray diagrams were therefore recorded for a range of reciprocal spacing $q=4\pi^*\sin\theta/\lambda$ of 0.03-1.8 Å$^{-1}$, in which $\theta$ is the scattering angle. The repetitive distances $d=2\pi/q$ should be between 200 Å and 3.5 Å. The samples were placed in 1.2-1.3 mm glass capillaries (Glas W. Müller, Germany) and introduced into a home-made capillary holder which can accommodate up to 20 capillaries at controlled temperature.

Surfactant System

The surfactant system used in a composition in accordance with the invention and which makes it possible to obtain the formation of a paracrystalline phase of lamellar type (Lβ) preferably comprises:
i) at least one nonionic surfactant with an HLB value at 25° C. of less than 8, the surfactant(s) with an HLB value at 25° C. of less than 8 preferably being chosen from nonionic surfactants, and
ii) at least one nonionic surfactant with an HLB value at 25° C. of greater than or equal to 8.

According to one particular embodiment, a composition according to the invention comprises a surfactant system comprising:
at least one nonionic surfactant with an HLB value at 25° C. of less than 8, and
at least one nonionic surfactant with an HLB value at 25° C. of greater than or equal to 8,
at least one from among the nonionic surfactant(s) with an HLB value at 25° C. of less than 8 and at least one from among the nonionic surfactant(s) with an HLB value at 25° C. of greater than or equal to 8 corresponding to formula (I) below:

$$(ALK-[C(O)]_a-[O]_b)_c-X \qquad (I)$$

in which formula (I):
ALK is a $C_7$-$C_{23}$, preferably $C_{11}$-$C_{21}$ and more preferentially $C_{15}$-$C_{17}$ alkyl group,
a and b are integers between 0 and 100, c is an integer between 1 and 100, in particular between 1 and 3, preferably equal to 1, a and b preferably being equal to 0,
X is a (poly)oxyalkylene group optionally substituted and/or terminated with a hydroxyl group, X preferably being an oxyethylene group $(CH_2CH_2O)_n$ or $(OCH_2CH_2)_n$ in which n is greater than or equal to 1, for example between 1 and 200, said (poly)oxyalkylene group preferably being a polyethylene glycol or being the result of at least one substitution of a hydroxyl group, preferably chosen from (poly)glycerols.

The group X is preferably chosen from:
i) HO-(ALK-O)$_z$—CH2-CH[(OALK)$_y$-OH]—CH2-(O-ALK)$_x$-(*)
in which:
ALK, which may be identical or different, represent a $C_1$-$C_6$ and in particular $C_1$-$C_4$ alkylene group, preferably ethylene,
x, y and z are an integer between 0 and 200, it being understood that x+y+z is other than 0, x+y+z preferably being inclusively between 1 and 150, in particular between 20 and 60;
ii) H-(ALK-O)$_x$-(*) and H—(O-ALK)$_x$-(*), preferably is H—(O-ALK)$_x$-(*)
in which:
ALK, which may be identical or different, represent a $C_1$-$C_6$ and in particular $C_1$-$C_4$ ethylene group, preferably ethylene,
x is an integer other than 0 and preferably between 1 and 200.

The nonionic surfactant(s) with an HLB value at 25° C. of less than 8 and the nonionic surfactant(s) with an HLB value at 25° C. of greater than or equal to 8 correspond(s) to formula (I') below:

$$ALK-(O-CH_2-CH_2)_n-OH \qquad (I')$$

in which formula (I'):
ALK is a $C_8$-$C_{24}$, preferably $C_{12}$-$C_{22}$ and more preferentially $C_{16}$-$C_{18}$ alkyl group,
n being an integer other than 0, between 1 and 200, preferably between 1 and 10, better still between 2 and 6 for the nonionic surfactant(s) with an HLB value at 25° C. of less than 8, and preferably between 20 and 200 for the nonionic surfactant(s) with an HLB value at 25° C. of greater than or less than 8.

The Griffin HLB (hydrophilic/lipophilic balance) value is defined in J. Soc. Cosm. Chem. 1954 (volume 5), pages 249-256. Reference may be made to the Kirk-Othmer Encyclopedia of Chemical Technology, volume 22, p. 333-432, 3rd edition, 1979, Wiley, for the definition of the emulsifying properties and functions of surfactants, in particular p. 347-377 of this reference.

The nonionic surfactant(s) with an HLB value at 25° C. of less than 8, preferably corresponding to formula (I), are present in a content of greater than or equal to 5% by weight relative to the total weight of the composition, preferably between 7% and 30%, preferably between 10% and 20% by weight relative to the total weight of the composition.

The nonionic surfactant(s) with an HLB value at 25° C. of greater than or equal to 8, preferably greater than or equal to 10, preferably corresponding to formula (I) are present in a content of greater than or equal to 5% by weight relative to the total weight of the composition, preferably between 7% and 30%, preferably between 10% and 20% by weight relative to the total weight of the composition.

The nonionic surfactant(s) with an HLB value at 25° C. of less than 8 and the nonionic surfactant(s) with an HLB value at 25° C. of greater than or equal to 8, both preferably corresponding to formula (I), are present in a total content of greater than or equal to 15%, in particular between 16% and 40% by weight, better still between 18% and 30% by weight, relative to the total weight of the composition.

The nonionic surfactant(s) with an HLB value at 25° C. of less than 8 and the nonionic surfactant(s) with an HLB value at 25° C. of greater than or equal to 8, both preferably corresponding to formula (I), are present in a respective total content such that the weight ratio of the nonionic surfactant(s) with an HLB value at 25° C. of less than 8 to the nonionic surfactant(s) with an HLB value at 25° C. of greater than or equal to 8, ranges from 1/5 to 5, preferably from 1/3 to 3, preferably from 2/3 to 3/2.

Nonionic Surfactant(s) with an HLB Value at 25° C. of Less than 8

The nonionic surfactant(s) with an HLB value, in the Griffin sense, at 25° C., of less than 8 may be advantageously chosen from:
esters and ethers of monosaccharides which are optionally (poly)oxyalkylenated, preferably (poly)oxyalkylenated;
esters of fatty acids, in particular of $C_8$-$C_{24}$ and preferably of $C_{16}$-$C_{22}$ fatty acids, and of polyol, which is optionally (poly)oxyalkylenated, preferably (poly)oxyalkylenated, in particular of (poly)oxyalkylenated glycerol or of (poly)oxyalkylenated sorbitol, preferably of (poly)oxyalkylenated glycerol;
alcohols which are optionally (poly)oxyalkylenated, preferably (poly)oxyalkylenated;
and mixtures thereof; preferably from among alcohols which are optionally (poly)oxyalkylenated, preferably (poly)oxyalkylenated, preferably comprising from 1 to 10 oxyethylene units.

The term "(poly)oxyalkylenated" means from 1 to 10 oxyethylene group (or units) and better still from 2 to 6 oxyethylene groups.

The at least one from among the nonionic surfactant(s) with an HLB value at 25° C. of less than 8 preferably comprises an alcohol which is optionally (poly)oxyalkylenated, preferably (poly)oxyalkylenated, comprising an ether of a $C_8$-$C_{24}$ fatty alcohol and of polyethylene glycol, said ether comprising from 1 to 10 and better still between 2 and 6 ethylene glycol units.

A composition according to the invention has a content of nonionic surfactant(s) with an HLB value, in the Griffin sense, at 25° C., of less than 8, of greater than or equal to 5% by weight relative to the total weight of the composition, preferably between 8% and 20% by weight relative to the total weight of the composition.

Nonionic Surfactant(s) with an HLB Value at 25° C. of Greater than or Equal to 8

The nonionic surfactant(s) with an HLB value, in the Griffin sense, at 25° C., of greater than or equal to 8 may advantageously be chosen from:

- (poly)oxyalkylenated, in particular oxyethylenated and/or oxypropylenated, glycerol ethers, which may comprise more than 10 oxyethylene and/or oxypropylene units, in particular from 15 to 200 units and better still from 15 to 100 oxyethylene and/or oxypropylene units;
- (poly)oxyalkylenated, in particular oxyethylenated and/or oxypropylenated, alcohols, which may comprise more than 10 oxyethylene and/or oxypropylene units, in particular from 15 to 200 units and better still from 15 to 100 oxyethylene and/or oxypropylene units, in particular ethoxylated fatty alcohols, especially of $C_8$-$C_{24}$ and preferably $C_{12}$-$C_{18}$, such as ethoxylated stearyl alcohol comprising 20 oxyethylene units (CTFA name: Steareth-20) such as Brij 78 sold by the company Uniqema, or ethoxylated cetearyl alcohol comprising 30 oxyethylene units (CTFA name: Ceteareth-30);
- esters of a (poly)oxyalkylenated fatty acid, in particular fatty acid esters, especially a $C_8$-$C_{24}$ and preferably $C_{16}$-$C_{22}$ fatty acid, and of polyethylene glycol (or PEG) (which may comprise more than 10 oxyethylene units, in particular from 15 to 200 units and better still from 15 to 100 oxyethylene units), such as PEG-50 stearate and PEG-40 monostearate sold under the name Myrj 52P® by the company Uniqema;
- esters of a fatty acid, especially a $C_8$-$C_{24}$ and preferably $C_{16}$-$C_{22}$ fatty acid, and of (poly)oxyalkylenated, in particular oxyethylenated and/or oxypropylenated glycerol ethers (which may comprise more than 10 oxyethylene and/or oxypropylene units, in particular from 15 to 200 units and better still from 15 to 100 oxyethylene and/or oxypropylene units), for instance glyceryl monostearate polyoxyethylenated with 200 oxyethylene units, sold under the name Simulsol 220 TM® by the company SEPPIC; glyceryl stearate polyoxyethylenated with 30 oxyethylene units, for instance the product Tagat S® sold by the company Goldschmidt, glyceryl oleate polyoxyethylenated with 30 oxyethylene units, for instance the product Tagat O® sold by the company Goldschmidt, glyceryl cocoate polyoxyethylenated with 30 oxyethylene units, for instance the product Varionic LI 13® sold by the company Sherex, glyceryl isostearate polyoxyethylenated with 30 oxyethylene units, for instance the product Tagat L® sold by the company Goldschmidt, and glyceryl laurate polyoxyethylenated with oxyethylene units, for instance the product Tagat I® from the company Goldschmidt;
- esters of a fatty acid, especially a $C_8$-$C_{24}$ and preferably $C_{16}$-$C_{22}$ fatty acid, and of (poly)oxyalkylenated, in particular oxyethylenated and/or oxypropylenated, sorbitol ethers (which may comprise more than 10 oxyethylene and/or oxypropylene units, in particular from 15 to 200 units and better still from 15 to 100 oxyethylene and/or oxypropylene units), for instance polysorbate 60 sold under the name Tween 60® by the company Uniqema;
- and mixtures thereof; preferably from (poly)oxyalkylenated alcohols preferably comprising more than 10 oxyethylene units, in particular from 15 to 200 units and better still from 15 to 100 oxyethylene (or ethylene glycol) units.

Preferably, a composition comprises at least one nonionic surfactant with an HLB value, in the Griffin sense, at 25° C., of greater than or equal to 8, preferably greater than or equal to 10, chosen from at least one $C_8$-$C_{24}$, preferably $C_{12}$-$C_{22}$ and more preferentially $C_{16}$-$C_{18}$ fatty alcohol ether of polyethylene glycol, said ether comprising more than 10 ethylene glycol units, better still between 15 and 200 ethylene glycol units.

Preferably, a composition in accordance with the invention is free of alkyl phosphates and in particular is free of cetyl phosphate.

Preferably, a composition in accordance with the invention is free of amphoteric surfactant(s).

Moreover, the surfactant system may comprise one or more co-surfactants chosen from fatty alcohols comprising from 10 to 26 carbon atoms, better still from 12 to 24 carbon atoms and even better still from 14 to 22 carbon atoms. However, this (these) co-surfactant(s) are not involved in the calculation of the total content of surfactant system in accordance with the invention.

Fillers

A composition according to the invention comprises at least one filler and in particular at least one spherical filler, more particularly at least one organic spherical filler.

The term "fillers" should be understood as meaning colourless or white solid particles of any form, which are in a form that is insoluble and dispersed in the medium of the composition. Mineral or organic in nature, they make it possible to confer softness, mattness and uniformity of makeup on the composition.

The fillers may or may not be surface-coated, and in particular they may be surface-treated with silicones, amino acids, fluoro derivatives or any other substance that promotes the dispersion and compatibility of the filler in the composition.

Such fillers are distinct from what is referred to in the next section as "colouring agents".

A composition according to the invention advantageously has a filler content of greater than or equal to 5% by weight, better still greater than or equal to 8% by weight, relative to the total weight of the composition, advantageously between 8% and 30% by weight, better still between 8% and 25% by weight, better still between 10% and 20% by weight, relative to the total weight of the composition.

The composition comprises at least one spherical filler. It may also comprise at least one lamellar filler.

Spherical Fillers

The term "spherical fillers" should be understood to mean fillers comprising at least one rounded general portion, preferably defining at least one sphere portion, preferably defining internally a cavity or a hollow.

Such fillers referred to as spherical may be perfectly spherical fillers, globular fillers, hemi-spherical fillers, bowl-shaped fillers or else horseshoe-shaped fillers.

The spherical filler(s) are preferably hollow, where appropriate being capable of absorbing and/or adsorbing at least partially the oily phase and more generally the fatty phase.

The spherical filler(s) in accordance with the invention are advantageously a sebum-absorbing particle or particles, having a sebum uptake. The term "sebum-absorbing particle" means a powder capable of absorbing and/or adsorbing sebum.

The sebum uptake corresponds to the amount of sebum absorbed and/or adsorbed by the particle. It is measured according to the wet point method as follows:

Method for Measuring Sebum Uptake of a Powder:

The sebum uptake of a powder is measured according to the method for determining the oil uptake of a powder described in standard NF T 30-022. It corresponds to the amount of sebum adsorbed onto the available surface of the powder, by measuring the wet point.

An amount m (in grams) of powder of between about 0.5 g and 5 g (the amount depends on the density of the powder) is placed on a glass plate and artificial sebum having the following composition is then added dropwise:

| | |
|---|---|
| triolein | 29% |
| oleic acid | 28.5% |
| oleyl oleate | 18.5% |
| squalene | 14% |
| cholesterol | 7% |
| cholesteryl palmitate | 3% |

After addition of 4 to 5 drops of artificial sebum, the artificial sebum is incorporated into the powder using a spatula, and addition of the artificial sebum is continued until conglomerates of artificial sebum and powder have formed. From this point, the artificial sebum is added at a rate of one drop at a time and the mixture is subsequently triturated with the spatula. The addition of artificial sebum is stopped when a firm, smooth paste is obtained. This paste must be able to be spread on the glass plate without cracking or forming lumps. The volume Vs (expressed in ml) of artificial sebum used is then noted.

The sebum uptake corresponds to the ratio Vs/m.

Advantageously, the spherical fillers in accordance with the invention have a sebum uptake greater than or equal to 10 ml/100 g, in particular greater than or equal to 20 ml/100 g, and in particular greater than or equal to 30 ml/100 g, preferably greater than or equal to 40 ml/100 g, and in particular inclusively between 45 and 1500 ml/100 g, or else between 45 and 300 ml/100 g.

The spherical filler(s) advantageously has (have) an average diameter, also called median diameter or number-average size, indicated by a value $D_{50}$, ranging from 0.05 μm to 50 μm, preferably ranging from 2 to 40 μm. This dimension $D_{50}$ is given by the statistical particle size distribution at half the population, termed D50.

The spherical filler(s) are present in a total content of greater than or equal to 5% by weight, relative to the total weight of the composition, for example between 8% and 30% by weight, relative to the total weight of the composition, preferably between 8% and 25% by weight, better still between 10% and 20% by weight.

The spherical filler(s) and the surfactant system in accordance with the invention are advantageously present in a respective total weight content such that the weight ratio of the spherical filler(s) to the surfactant system is greater than or equal to 1/10, preferably between 1/5 and 6/5.

The spherical filler(s) and the nonionic surfactant(s) with an HLB value of greater than or equal to 8 advantageously present in the composition in a respective total content such that the weight ratio of the spherical filler(s) to the nonionic surfactant(s) with an HLB value of greater than or equal to 8 ranges from 1/20 to 1, preferably from 1/10 to 2/3.

The spherical filler(s) and the nonionic surfactant(s) with an HLB value of less than 8 advantageously present in the composition in a respective total content such that the weight ratio of the spherical filler(s) to the nonionic surfactant(s) with an HLB value of less than 8 ranges from 1/20 to 1, preferably from 1/10 to 2/3.

The spherical fillers may be inorganic or organic, preferably organic.

As non-limiting illustrations of fillers according to the invention, mention may be made most particularly of the particles below.

The spherical fillers are advantageously chosen from:
silica powders;
powders of acrylic (co)polymers, and derivatives thereof, in particular powders of acrylate (co)polymer, and derivatives thereof, advantageously chosen from a polymethyl methacrylate powder, a polymethyl methacrylate/ethylene glycol dimethacrylate powder, a polyallyl methacrylate/ethylene glycol dimethacrylate powder, an ethylene glycol dimethacrylate/lauryl methacrylate copolymer powder, a powder of acrylate/alkyl acrylate copolymer which is optionally crosslinked, expanded hollow particles of acrylonitrile (co)polymer, and a mixture or mixtures thereof;
polyurethane powders;
silicone powders advantageously chosen from a polymethylsilsesquioxane powder, an organopolysiloxane elastomer powder coated with silicone resin, a powder of organosilicone particles;
powders of polyamides, such as Nylon®, in particular Nylon 12;
and a mixture or mixtures thereof.

Such spherical fillers may be coated with a hydrophobic treatment agent. The hydrophobic treatment agent can be chosen from fatty acids, such as stearic acid; metal soaps, such as aluminium dimyristate or the aluminium salt of hydrogenated tallow glutamate; amino acids; N-acylamino acids or their salts; lecithin, isopropyl-triisostearyl titanate, and mixtures thereof. The N-acylamino acids can comprise an acyl group containing from 8 to 22 carbon atoms, for instance a 2-ethylhexanoyl, caproyl, lauroyl, myristoyl, palmitoyl, stearoyl or cocoyl group. The salts of these compounds can be the aluminium, magnesium, calcium, zirconium, zinc, sodium or potassium salts. The amino acid can, for example, be lysine, glutamic acid or alanine. The term "alkyl" mentioned in the compounds cited above denotes in particular an alkyl group having from 1 to 30 carbon atoms and preferably having from 5 to 16 carbon atoms.

More particularly, the spherical filler(s) are advantageously chosen from powders of acrylic (co)polymers, and derivatives thereof, in particular a polymethyl methacrylate powder, polyurethane powders, in particular a hexamethylene diisocyanate/trimethylol hexyl lactone copolymer powder, and a mixture or mixtures thereof.

Silica Powders

Mention may be made, as silica powder, of:
the porous silica microspheres sold under the name Silica Beads SB-700 by the company Miyoshi; Sunsphere® H51, Sunsphere® H33 by the company Asahi Glass;
the polydimethylsiloxane-coated amorphous silica microspheres sold under the name SA Sunsphere® H33 or SA Sunsphere® H53 by the company Asahi Glass.

Powders of Acrylic (Co)Polymers, and Derivatives Thereof

Mention may be made, as acrylic (co)polymer powder, and in particular acrylate (co)polymer powder, of:

the polymethyl methacrylate powders sold under the name Covabead® LH85 by the company Wackherr;

the polymethyl methacrylate/ethylene glycol dimethacrylate powders sold under the name Dow Corning 5640 Microsponge® Skin Oil Adsorber by the company Dow Corning and the name Ganzpearl® GMP-0820 by the company Ganz Chemical;

the polyallyl methacrylate/ethylene glycol dimethacrylate powders sold under the names Polypore® L200 and Polypore® E200 by the company Amcol Health and Beauty Solutions Inc.;

the ethylene glycol dimethacrylate/lauryl methacrylate copolymer powders sold under the name Polytrap® 6603 by the company Dow Corning;

the crosslinked acrylate/ethylhexyl acrylate copolymer powders sold under the name Techpolymer ACP-8C by the company Sekisui Plastics;

the expanded hollow particles of acrylonitrile (co)polymer sold under the name Expancel by the company Expancel;

and a mixture or mixtures thereof.

The polymethyl methacrylates are generally in the form of hollow or filled white spherical particles of which the number-average size D50 is generally on the micrometer scale, and in particular ranges from 5 to 20 microns and generally ranges from 7 to 15 microns.

As a non-limiting illustration of the polymethyl methacrylates that are suitable for the invention, mention may particular be made of the polymethyl methacrylate particles sold by the company Wackherr under the name Covabead LH 85 and those sold by the company Nihon Junyaku under the name Jurymer MB1.

The expanded hollow particles of acrylonitrile (co)polymer are thus derived from at least one acrylonitrile polymer or copolymer. They are made of any expanded acrylonitrile polymer or copolymer, which is non-irritant to the skin.

These particles are advantageously spherical in shape. The density of the particles is chosen in the range from 15 kg/m$^3$ to 200 kg/m$^3$, better still from 30 kg/m$^3$ to 120 kg/m$^3$ and even better still from 40 kg/m$^3$ to 80 kg/m$^3$. To obtain this low density, use is advantageously made of expanded polymer or copolymer particles, based on acrylonitrile and preferably on an acrylic or styrene and/or vinylidene chloride monomer.

It is possible, for example, to use a copolymer containing: from 0% to 60% of units derived from vinylidene chloride, from 20% to 90% of units derived from acrylonitrile and 0% to 50% of units derived from an acrylic or styrene monomer, the sum of the percentages (by weight) being equal to 100%. The acrylic monomer is, for example, a methyl or ethyl acrylate or methacrylate. The styrene monomer is, for example, methylstyrene or styrene.

Preferably, the particles used in the present invention are hollow particles of an expanded copolymer of vinylidene chloride and acrylonitrile, an expanded copolymer of vinylidene chloride, acrylonitrile and methacrylate, or a mixture thereof. These particles may be dry or hydrated.

The particles of the invention may be obtained, for example, according to the processes of patents and patent applications EP-56219, EP-348 372, EP-486 080, EP-320 473, EP-1 12 807 and U.S. Pat. No. 3,615,972.

The internal cavity of the particles contains in principle a gas which may be air, nitrogen or a hydrocarbon such as isobutane or isopentane, preferably isobutane.

Advantageously, the particles of the invention have a particle size ranging from 1 µm to 80 µm, better still ranging from 10 µm to 50 µm and better still from 20 µm to 40 µm.

The particles that may be used in the invention are, for example, microspheres of expanded terpolymer of vinylidene chloride, acrylonitrile and methacrylate, sold under the brand name Expancel by the company Expancel under the references 551 DE 40 (particle size of approximately 40 µm), 551 DE (particle size of approximately 20 µm and density of approximately 65 kg/m$^3$), 551 DE 12 (particle size of approximately 12 µm), 551 DE 80 (particle size of approximately 80 µm) and 461 DE 50 (particle size of approximately 50 µm). It is also possible to use microspheres formed from the same expanded terpolymer with a particle size of approximately 18 µm and a density of approximately 70 kg/m$^3$, referred to below as EL23, or with a particle size of approximately 34 µm and a density of approximately 20 kg/m$^3$, referred to below as EL 43.

The expanded acrylonitrile (co)polymer hollow particles are preferably chosen from an expanded copolymer of vinylidene chloride and acrylonitrile, an expanded copolymer of vinylidene chloride, acrylonitrile and methacrylate, and a mixture thereof.

Polyurethane Powders

The polyurethane powder is advantageously a hexamethylene diisocyanateitrimethylol hexyl lactone copolymer powder.

Advantageously, the composition according to the invention contains a polyurethane powder that is not film-forming, i.e. it does not form a continuous film when it is deposited onto a support such as the skin.

Such a polyurethane powder is in particular sold under the names Plastic Powder D-400, Plastic Powder D-800 and Plastic Powder T-75 by the company Toshiki.

Another polyurethane powder that may be used is the one sold under the name Plastic Powder CS-400 by the company Toshiki.

Silicone Powders

The silicone powder(s) are advantageously chosen from a polymethylsilsesquioxane powder, an organopolysiloxane elastomer powder coated with silicone resin, and a powder a powder of organosilicone particles.

Polymethylsilsesquioxane Powder

The composition according to the invention comprises at least one silicone filler and preferably this silicone filler is a polymethylsilsesquioxane powder.

The presence of such a filler makes it possible especially to improve the persistence, and in particular the persistence of the colour of the deposit on the skin or the lips produced with the composition, without losing gloss. The composition according to the invention also allows the production of a sparingly tacky or non-tacky deposit.

As polymethylsilsesquioxane powder, use may be made of the product sold under the name Tospearl by the company Momentive Performance Materials, and in particular under the reference Tospearl 145 A.

Organopolysiloxane Elastomer Powder Coated with Silicone Resin

The composition according to the invention comprises at least one organopolysiloxane elastomer powder coated with silicone resin, in particular silsesquioxane resin, as described, for example, in U.S. Pat. No. 5,538,793, the content of which is incorporated by way of reference.

Such elastomer powders are sold under the names KSP-100, KSP-101, KSP-102, KSP-103, KSP-104 and KSP-105 by the company Shin-Etsu, and have the INCI name: vinyl dimethicone/methicone silsesquioxane crosspolymer.

Preferably, the organopolysiloxane elastomer powder coated with silicone resin is a compound having the INCI name: Vinyl Dimethicone/Methicone Silsesquioxane Crosspolymer.

Mention may be made, as silicone elastomer powder, of the powders sold under the names Trefil® Powder E-505C and Trefil® Powder E-506C by the company Dow Corning.

Oroanosilicone Particles

According to one particular embodiment of the invention, "bowl"-shaped hollow sphere portions are used. Said sphere portions can be obtained as described in application JP-2003 128 788, and horseshoe-shaped hollow sphere portions are also described in application JP-A-2000-191789, or else in application EP 1 579 841.

As concave particles of sphere portions that may be used according to the invention, mention may in particular be made of:

bowl-shaped particles consisting of the crosslinked organosilicone Tak-110 (methylsilanol/silicate crosslinked polymer) from the company Takemoto Oil & Fat, of width 2.5 µm, height 1.2 µm and thickness 150 nm (particles sold under the name NLK-506 by the company Takemoto Oil & Fat);

bowl-shaped particles consisting of the crosslinked organosilicone Tak-110 (methylsilanol/silicate crosslinked polymer) from the company Takemoto Oil & Fat, of width 2.5 µm, height 1.5 µm and thickness 350 nm;

bowl-shaped particles consisting of the crosslinked organosilicone Tak-110 (methylsilanol/silicate crosslinked polymer) from the company Takemoto Oil & Fat, of width 0.7 µm, height 0.35 µm and thickness 100 nm;

bowl-shaped particles consisting of the crosslinked organosilicone Tak-110 (methylsilanol/silicate crosslinked polymer) from the company Takemoto Oil & Fat, of width 7.5 µm, height 3.5 µm and thickness 200 nm.

Polyamide Powders

Preferably, the polyamide particles have a number-average size ranging from 50 nm to 350 microns, better still between 100 nm and 100 microns and even more preferentially between 0.5 and 100 microns.

The polyamide particles are chosen from particles of nylon 12.

As polyamide powder, mention may also be made of the nylon powders sold under the name Orgasol® 2002 EXS NAT COS by the company Arkema.

Lamellar Fillers

The pulverulent phase may comprise at least one lamellar filler.

The lamellar filler(s) are preferably mineral.

The lamellar filler(s) that can be used in the compositions according to the invention are preferably chosen from talc, natural or synthetic mica, certain silicas, clays such as magnesium aluminium silicates, perlite particles, kaolin, bentone, calcium carbonate and magnesium hydrogen carbonate, hydroxyapatite, boron nitride, fluorphlogopite, an N-lauroyl lysine powder, and a mixture or mixtures thereof.

Perlite Particles

Perlite is generally obtained from natural glass of volcanic origin, of light-grey or glossy black colour, resulting from the rapid cooling of lava, and which is in the form of small particles resembling pearls. When heated above 800° C., perlite has the particular feature of losing the water it contains and of adopting a porous expanded form (representing from four to twenty times its initial volume), enabling it to absorb large amounts of liquid, in particular of oil and water. It then has a white colour.

Perlite, which is of mineral origin, is directly extracted from the ground and then finely ground to obtain a very fine white powder: perlite powder or perlite particles.

Perlite particles are thus particles of amorphous mineral materials, which are advantageously expanded, derived from at least one volcanic rock.

These particles comprise at least two elements chosen from silicon, aluminium and magnesium.

More particularly, these mineral materials are obtained by thermal expansion of a volcanic or "effusive" rock comprising from 1% to 10% by weight of water and preferably 1% to 5% by weight of water and less than 10% by weight of crystalline rock relative to the total weight of the rock composition and preferably followed by grinding. The temperature of the expansion process may range from 700 to 1500° C. and preferably from 800 to 1100° C. The expansion process described in U.S. Pat. No. 5,002,698 may in particular be used.

Volcanic or "effusive" rocks are generally produced by the rapid cooling of liquid magma in contact with air or water (quenching phenomenon giving a hyaline rock). The volcanic rocks that may be used according to the present invention are chosen from those defined according to the Streckeisen classification (1974). Among these volcanic rocks, mention may be made in particular of trachytes, latites, andesites, basalts, rhyolites and dacites. Rhyolites and dacites are particularly suitable for use, and even more particularly rhyolites.

The perlite particles that may be used according to the invention are preferably aluminosilicates of volcanic origin. They advantageously have the following composition:

70.0-75.0% by weight of silica $SiO_2$
12.0-15.0% by weight of aluminium oxide $Al_2O_3$
3.0-5.0% of sodium oxide $Na_2O$
3.0-5.0% of potassium oxide $K_2O$
0.5-2% of iron oxide $Fe_2O_3$
0.2-0.7% of magnesium oxide MgO
0.5-1.5% of calcium oxide CaO
0.05-0.15% of titanium oxide $TiO_2$ In the implementation of the present invention, the perlite undergoes a first milling step so as to form perlite particles, and is dried and then calibrated. The product obtained, known as perlite ore, is grey-coloured and has a size of the order of 100 µm. The perlite ore is subsequently expanded (1000° C./2 seconds) to give more or less white particles. When the temperature reaches 850-900° C., the water trapped in the structure of the material evaporates and brings about the expansion of the material, with respect to its original volume. The expanded perlite particles in accordance with the invention may be obtained via the expansion process described in patent U.S. Pat. No. 5,002,698.

Preferably, the perlite particles used are then milled in a second milling step in order further to reduce the size of the perlite particles used; in this case, they are referred to as expanded milled perlite (EMP). They preferably have a particle size defined by a median diameter $D_{50}$ ranging from 0.5 to 50 µm and preferably from 1 to 40 µm.

Preferentially, the perlite particles have a platelet shape; they are consequently usually called lamellar fillers, as opposed to spherical fillers, of globular shape.

The perlite particles advantageously have a coefficient of expansion of from 2 to 70.

Preferentially, the perlite particles have an untamped density at 25° C. ranging from 10 to 400 kg/m$_3$ (standard DIN 53468) and preferably from 10 to 300 kg/m$^3$.

According to one particular embodiment of the invention, the perlite particles have a silica content of greater than or equal to 65% by weight relative to the total weight of the composition of the material. According to one particular embodiment of the invention, the perlite particles have a spontaneous pH, measured at 25° C. in a dispersion in water at 10% by weight, ranging from 6 to 8.

Preferably, the expanded perlite particles according to the invention have a water absorption capacity, measured at the wet point, ranging from 200% to 1500% and preferably from 250% to 800%.

The perlite particles used according to the invention are in particular commercially available from the company World Minerals under the trade name Perlite P1430, Perlite P2550, Perlite P2040 or OpTiMat™ 1430 OR or 2550 OR.

As representatives of such fillers preferably used in the context of the present invention, mention may be made in particular of: talc, mica, fluorphlogopite, perlite, clays such as magnesium aluminium silicate, an N-lauroyl lysine powder, and a mixture or mixtures thereof.

The lamellar filler(s) are advantageously present in a composition in accordance with the present invention in a total content of greater than or equal to 5% by weight, relative to the total weight of the composition, for example between 8% and 30% by weight, relative to the total weight of the composition, preferably between 8% and 25% by weight, better still between 10% and 20% by weight.

Dyes

The compositions in accordance with the invention comprise at least one dye.

This (or these) dye(s) are preferably chosen from pulverulent materials, liposoluble dyes and water-soluble dyes, and mixtures thereof.

Preferably, the compositions according to the invention comprise at least one pulverulent dye. The pulverulent dyes may be chosen from pigments and nacres, and preferably from pigments.

The pigments may be white or coloured, inorganic and/or organic, and coated or uncoated. Among the inorganic pigments, mention may be made of metal oxides, in particular titanium dioxide, optionally surface-treated, zirconium, zinc or cerium oxide, and also iron, titanium or chromium oxide, manganese violet, ultramarine blue, chromium hydrate and ferric blue. Among the organic pigments that may be mentioned are carbon black, pigments of D&C type and lakes based on cochineal carmine or on barium, strontium, calcium or aluminium.

The nacres may be chosen from white nacreous pigments such as mica coated with titanium or with bismuth oxychloride, coloured nacreous pigments such as titanium mica with iron oxides, titanium mica with in particular ferric blue or chromium oxide, titanium mica with an organic pigment of the abovementioned type, and also nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto.

Preferably, the pigments contained in the compositions according to the invention are chosen from metal oxides.

These dyes may be present in a content ranging from 0.01% to 30% by weight relative to the total weight of the composition and in particular from 6% to 22% by weight relative to the total weight of the composition.

Preferably, the dye(s) are chosen from one or more metal oxides that are present in a content of greater than or equal to 2% by weight relative to the total weight of the composition, and advantageously inclusively between 6% and 22% by weight relative to the total weight of the composition.

Wax(es)

The wax(es) are generally a lipophilic compound that is solid at ambient temperature (25° C.), with a solid/liquid reversible change of state, having a melting point of greater than or equal to 30° C., which may be up to 200° C. and in particular up to 120° C.

For the purposes of the invention, the melting point corresponds to the temperature of the most endothermic peak observed on thermal analysis (DSC) as described in standard ISO 11357-3; 1999. The melting point of the wax may be measured using a differential scanning calorimeter (DSC), for example the calorimeter sold under the name DSC Q2000 by the company TA Instruments.

Preferably, the waxes have a heat of fusion ΔHf of greater than or equal to 70 J/g.

Preferably, the waxes comprise at least one crystallizable part, which is visible by X-ray observation.

The measurement protocol is as follows:

A 5 mg sample of wax placed in a crucible is subjected to a first temperature increase from −20° C. to 100° C., at a heating rate of 10° C./minute, and then is cooled from 120° C. to −20° C. at a cooling rate of 10° C./minute and finally subjected to a second temperature increase from −20° C. to 120° C. at a heating rate of 5° C./minute. During the second temperature increase, the following parameters are measured:

the melting point (Mp) of the wax, as mentioned previously corresponding to the temperature of the most endothermic peak of the melting curve observed, representing the variation of the difference in power absorbed as a function of the temperature, ΔHf: the heat of fusion of the wax, corresponding to the integral entire melting curve obtained. This heat of fusion of the wax is the amount of energy required to make the compound change from the solid state to the liquid state. It is expressed in J/g.

The wax(es) may be hydrocarbon-based wax(es), fluoro wax(es) and/or silicone wax(es) and may be of plant, mineral, animal and/or synthetic origin.

When present, the wax(es) are present in a total content preferably of strictly less than 10% by weight, better still less than 5% by weight, or even less than 2% by weight, relative to the total weight of the composition.

Hard Wax

The composition may comprise at least one hard wax.

For the purposes of the present invention, the term "hard wax" means a wax with a melting point ranging from 65 to 120° C. and more preferentially between 70 and 100° C.

Advantageously, for the purposes of the present invention, the term "hard" wax means a wax having, at 20° C., a hardness of greater than 5 MPa, in particular ranging from 5 to 30 MPa, preferably greater than 6 MPa and better still ranging from 6 to 25 MPa.

To take these hardness measurements, the wax is melted at a temperature equal to the melting point of the wax+20° C. To do this, 30 g of wax are placed in a 100 ml beaker 50 mm in diameter, which is itself placed on a magnetic-stirring hotplate.

An amount of about 15 g of molten wax is poured into a stainless-steel container 80 mm in diameter and 15 mm deep preheated to 45° C. in an oven. The wax is then left to recrystallize in a room thermostatically maintained at 20° C. for 24 hours before taking the measurement.

The mechanical properties of the wax or of the mixture of waxes are determined in a room thermostatically maintained at 20° C., using the texturometer sold under the name TA-XT2i by the company Swantech, equipped with a stainless-steel cylinder 2 mm in diameter.

The measurement comprises three steps: a first step after automatic detection of the surface of the sample, where the spindle moves at a measuring speed of 0.1 mm/s, and penetrates into the wax to a penetration depth of 0.3 mm, and the software notes the maximum force value reached; a second "relaxation" step where the spindle remains at this position for one second and the force is noted after 1 second of relaxation; finally, a third "withdrawal" step in which the spindle returns to its initial position at a speed of 1 mm/s, and the probe withdrawal energy (negative force) is noted.

The hardness value corresponds to the maximum measured compression force in newtons divided by the area of the texturometer cylinder, expressed in $mm^2$, in contact with the wax. The hardness value obtained is expressed in megapascals or MPa.

As examples of hard wax, mention may be made in particular of carnauba wax, candelilla wax, the wax Bis-PEG-12 Dimethicone Candelillate, for instance Siliconyl Candelilla Wax sold by the company Koster Keunen, hydrogenated jojoba wax, for instance the product sold by the company Desert Whale, hydrogenated palm oil such as the product sold by the company SIO, rice bran wax, sumach wax, ceresin waxes, laurel wax, Chinese insect wax, shellac wax, hydrogenated olive oil such as Waxolive from the company Soliance, the waxes obtained by hydrogenation of olive oil esterified with C12 to C18 fatty-chain alcohols, such as the products sold by the company Sophim under the trade names Phytowax Olive 12L44, 14L48, 16L55 and 18L57, the waxes obtained by hydrogenation of castor oil esterified with cetyl or behenyl alcohol, for instance the products sold under the names Phytowax Ricin 16L64 and Phytowax Ricin 22L73 by the company Sophim, hydrogenated camellina wax, ouricury wax, montan wax, ozokerite waxes, for instance Wax SP 1020 P sold by the company Strahl & Pitsch, microcrystalline waxes, for instance the product sold under the trade name Microwax HW by the company Paramelt, lauric, palmitic, cetylic and stearic acid triglycerides (INCI name: hydrogenated cocoyl glycerides), for instance the product sold under the trade name Softisan 100 by the company Sasol, polymethylene waxes, for instance the product sold under the trade name Cirebelle 303 by the company Sasol, polyethylene waxes, for instance the products sold under the trade names Performalene 400 polyethylene, Performalene 655 polyethylene and Performalene 500-L polyethylene by the company New Phase Technologies, alcohol-polyethylene waxes, for instance the product sold under the name Performacol 425 Alcohol by the company Bareco, the 95/5 ethylene/acrylic acid copolymer sold under the trade name Wax AC 540 by the company Honeywell, hydroxyoctacosanyl hydroxystearate, for instance the product sold under the trade name Elfacos C 26 by the company Akzo, octacosanyl stearate, for instance the product sold under the name Kester Wax K 82 H by the company Koster Keunen, stearyl stearate, for instance the product sold under the name Liponate SS by the company Lipo Chemicals, pentaerythrityl distearate, for instance the product sold under the name Cutina PES by the company Cognis, the mixture of dibehenyl adipate, dioctadecyl adipate and dieicosanyl adipate (INC name: C18-22 dialkyl adipate), the mixture of dilauryl adipate and ditetradecyl adipate (INCI name: C12-14 dialkyl adipate), the mixture of dioctadecyl sebacate, didocosyl sebacate and dieicosyl sebacate (INCI name: C18-22 dialkyl sebacate), the mixture of dioctadecyl octadecanedioate, didocosyl octanedioate and dieicosyl octanedioate (INCI name: C18-22 dialkyl octanedioate, for instance the products sold by the company Cognis, pentaerythrityl tetrastearate, for instance Liponate PS-4 from the company Lipo Chemicals, tetracontanyl stearate, for instance Kester Wax K76 H from the company Koster Keunen, stearyl benzoate, for instance Finsolv 116 from the company Finetex, behenyl fumarate, for instance Marrix 222 from the company Akzo Bernel, bis(1,1,1-trimethylolpropane) tetrastearate, for instance the product offered under the name Hest 2T-4S by the company Heterene, didotriacontanyl distearate, for instance Kester Wax K82D from the company Koster Keunen, polyethylene glycol montanate containing 4 oxyethylene units (PEG-4), for instance the product sold under the trade name Clariant Licowax KST1, hexanediol disalicylate, for instance Betawax RX-13750 sold by the company CP Hall, dipentaerythrityl hexastearate, for instance the product sold under the trade name Hest 2P-6S by the company Heterene, ditrimethylolpropane tetrabehenate, for instance the product sold under the trade name Hest 2T-4B by the company Heterene, jojoba esters, for instance the product sold under the trade name Floraester HIP by the company Floratech, mixtures of linear carboxylic acid (C20-40)/saturated hydrocarbons (INCI name: C20-40 acid polyethylene), for instance Performacid 350 acid from the company New Phase Technologies, synthetic wax of Fischer-Tropsch type, such as the product sold under the reference Rosswax 100 by the company Ross, stearyl alcohol, behenyl alcohol, dioctadecyl carbonate, for instance Cutina KE 3737, sucrose polybehenate, for instance Crodaderm B from the company Croda, and mixtures thereof.

Use may also be made of the waxes mentioned above in the form of commercially available mixtures, for example under the names Koster KPC-56 (mixture of 87.5% by weight of cetyl stearate, 7.5% by weight of behenyl alcohol and 5% by weight of palm kernel glycerides), KPC-60 (mixture of 87.5% by weight of stearyl stearate, 7.5% by weight of behenyl alcohol and 5% by weight of palm kernel glycerides), KPC-63 (mixture of 87.5% by weight of behenyl stearate, 7.5% by weight of behenyl alcohol and 5% by weight of palm kernel glycerides) and KPC-80 (mixture of 86% by weight of synthetic beeswax, 7.5% of hydrogenated plant oil and 6.5% by weight of behenyl alcohol) from the company Koster Keunen.

Use is preferably made of waxes of plant origin such as carnauba wax, candelilla wax, hydrogenated jojoba wax, sumach wax, the waxes obtained by hydrogenation of olive oil esterified with C12 to C18 fatty-chain alcohols sold by the company Sophim in the Phytowax range (12L44, 14L48, 16L55 and 18L57), rice bran wax, stearyl and behenyl alcohols, laurel wax or ouricury wax.

The hard wax(es) are preferably polar.

The term "polar" wax means a wax whose solubility parameter calculated above its melting point 6, is other than 0 $(J/cm^3)^{1/2}$.

In particular, the term "polar wax" means a wax whose chemical structure is formed essentially from, or even constituted of, carbon and hydrogen atoms, and comprising at least one highly electronegative heteroatom such as an oxygen, nitrogen, silicon or phosphorus atom.

The definition and calculation of the solubility parameters in the Hansen three-dimensional solubility space are described in the article by C. M. Hansen: "The three dimensional solubility parameters" J. Paint Technol. 39, 105 (1967).

According to this Hansen space:

$\delta_D$ characterizes the London dispersion forces derived from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a = (\delta_p^2 + \delta_h^2)^{1/2}$ The parameters $\delta_p$, $\delta_h$, $\delta_D$ and $\delta_a$ are expressed in $(J/cm^3)^{1/2}$.

When a composition according to the invention comprises at least one hard wax, the total content of hard wax(es) is preferably strictly less than 10% by weight, better still less than 5% by weight, or even less than 2% by weight, relative to the total weight of the composition.

According to one advantageous embodiment, the composition according to the invention is free of hard wax(es).

A composition according to the invention may comprise at least one soft wax, i.e. of which the melting point is strictly less than 50° C., and optionally of which the hardness is strictly less than 5 MPa.

However, a composition according to the invention preferably comprises less than 10% by weight of soft wax(es), preferably less than 5% by weight of soft wax(es), or even less than 2% by weight of soft wax(es), and even more preferentially is free of soft wax(es).

Film-Forming Polymer(s)

The composition according to the invention comprises at least one aqueous dispersion of film-forming polymer particles and optionally at least one additional film-forming polymer (not present in the form of an aqueous dispersion of particles, such as a water-soluble film-forming polymer).

In the present patent application, the term "film-forming polymer" means a polymer that is capable, by itself or in the presence of an auxiliary film-forming agent, of forming a macroscopically continuous deposit, and preferably a cohesive deposit, and even better still a deposit of which the cohesion and the mechanical properties are such that said deposit can be isolated and manipulated individually, for example when said deposit is prepared by pouring onto a non-stick surface such as a Teflon-coated or silicone-coated surface.

A composition according to the invention preferably comprises a total solids content of film-forming polymer(s) of greater than or equal to 5% by weight, preferably greater than or equal to 10% by weight, relative to the total weight of the composition, and better still greater than or equal to 12% by weight, relative to the total weight of the composition.

A composition according to the invention preferably comprises a total solids content of film-forming polymer(s) ranging from 10% to 30% by weight and better still from 12% to 25% relative to the total weight of the composition.

The composition according to the invention preferably comprises more specifically at least one aqueous dispersion of particles formed from one or more film-forming polymers.

It may also comprise at least one water-soluble film-forming polymer. Thus, a composition may comprise at least one additional film-forming polymer, different from the film-forming polymer particles present in aqueous dispersion form. The content of these "water-soluble" additional film-forming polymer(s) is preferably less than or equal to 10% by weight relative to the total weight of the composition, even more preferentially less than or equal to 5% by weight and better still less than or equal to 2% by weight relative to the total weight of the composition.

Film-Forming Polymer(s) in Aqueous Dispersion

Such a film-forming polymer present in said preparation of the composition in the form of particles in aqueous dispersion is generally known as a (pseudo)latex, i.e. a latex or psuedolatex. Techniques for preparing these dispersions are well known to those skilled in the art.

A dispersion that is suitable for use in the invention may comprise one or more types of particle, these particles possibly varying as regards their size, their structure and/or their chemical nature.

A composition according to the invention may comprise a total solids content of particles of film-forming polymer(s) in aqueous dispersion form of greater than or equal to 5% by weight, or even greater than or equal to 10% by weight, relative to the total weight of the composition.

Advantageously, a composition according to the invention comprises a total solids content of particles of film-forming polymer(s) in aqueous dispersion form of greater than or equal to 12% by weight relative to the total weight of the composition and preferably greater than or equal to 15% by weight relative to the total weight of the composition.

A composition according to the invention preferably comprises a total solids content of particles of film-forming polymer(s) ranging from 10% to 30% by weight and better still from 12% to 25% by weight relative to the total weight of the composition.

The total content of particles of film-forming polymer(s) present in aqueous dispersion form is preferably greater than or equal to 20% by weight, preferentially greater than or equal to 30%, preferably greater than 40% by weight, relative to the total weight of the particles.

These particles may be of anionic, cationic or neutral nature and may constitute a mixture of particles of different natures.

Among the film-forming polymers that may be used in the composition of the present invention, mention may be made of synthetic polymers, of free-radical type or of polycondensate type, and polymers of natural origin, and mixtures thereof. In general, these polymers may be statistical polymers, block copolymers of A-B type, of A-B-A or also ABCD, etc. multiblock type, or even grafted polymers.

Free-Radical Film-Forming Polymer

The term "free-radical polymer" means a polymer obtained by polymerization of unsaturated and in particular ethylenically unsaturated monomers, each monomer being capable of homopolymerizing (unlike polycondensates).

The film-forming polymers of free-radical type may in particular be acrylic and/or vinyl homopolymers or copolymers.

The vinyl film-forming polymers may result from the polymerization of ethylenically unsaturated monomers containing at least one acid group and/or esters of these acid monomers and/or amides of these acid monomers.

Ethylenically unsaturated monomers containing at least one acid group or monomer bearing an acid group that may be used include $\alpha,\beta$-ethylenic unsaturated carboxylic acids such as acrylic acid, methacrylic acid, crotonic acid, maleic acid or itaconic acid. (Meth)acrylic acid and crotonic acid are in particular used, and more particularly (meth)acrylic acid.

The esters of acid monomers are advantageously chosen from (meth)acrylic acid esters (also known as (meth)acrylates), in particular (meth)acrylates of an alkyl, in particular of a $C_1$-$C_{20}$ and more particularly $C_1$-$C_8$ alkyl, (meth)

acrylates of an aryl, in particular of a $C_6$-$C_{10}$ aryl, and (meth)acrylates of a hydroxyalkyl, in particular of a $C_2$-$C_6$ hydroxyalkyl.

Among the alkyl (meth)acrylates that may be mentioned are methyl methacrylate, ethyl methacrylate, butyl methacrylate, isobutyl methacrylate, 2-ethylhexyl methacrylate and lauryl methacrylate.

Among the hydroxyalkyl (meth)acrylates that may be mentioned are hydroxyethyl acrylate, 2-hydroxypropyl acrylate, hydroxyethyl methacrylate and 2-hydroxypropyl methacrylate.

Among the aryl (meth)acrylates that may be mentioned are benzyl acrylate and phenyl acrylate.

The (meth)acrylic acid esters are in particular alkyl (meth) acrylates.

According to the present invention, the alkyl group of the esters may be either fluorinated or perfluorinated, i.e. some or all of the hydrogen atoms of the alkyl group are substituted with fluorine atoms.

Mention may be made, as amides of the acid monomers, for example, of (meth)acrylamides and in particular N-alkyl (meth)acrylamides, in particular N—($C_2$-$C_{12}$ alkyl)(meth) acrylamides. Among the N-alkyl(meth)acrylamides that may be mentioned are N-ethylacrylamide, N-t-butylacrylamide and N-t-octylacrylamide.

The vinyl film-forming polymers may also result from the homopolymerization or copolymerization of monomers chosen from vinyl esters and styrene monomers. In particular, these monomers may be polymerized with acid monomers and/or esters thereof and/or amides thereof, such as those mentioned previously.

Examples of vinyl esters that may be mentioned are vinyl acetate, vinyl neodecanoate, vinyl pivalate, vinyl benzoate and vinyl t-butylbenzoate.

Styrene monomers that may be mentioned include styrene and α-methylstyrene.

The list of monomers given is not limiting, and it is possible to use any monomer known to those skilled in the art included in the categories of acrylic and vinyl monomers (including monomers modified with a silicone chain).

Vinyl polymers that may also be used include silicone acrylic polymers.

Mention may also be made of polymers resulting from free-radical polymerization of one or more free-radical monomers inside and/or partially at the surface of pre-existing particles of at least one polymer chosen from the group consisting of polyurethanes, polyureas, polyesters, polyesteramides and/or alkyds. These polymers are generally referred to as "hybrid polymers".

Polycondensate

As film-forming polymer of polycondensate type, mention may be made of anionic, cationic, nonionic or amphoteric polyurethanes, acrylic polyurethanes, polyvinylpyrrolidone-polyurethanes, polyester-polyurethanes, polyether-polyurethanes, polyureas, polyurea/polyurethanes and silicone polyurethanes, and mixtures thereof.

The film-forming polyurethane may be, for example, an aliphatic, cycloaliphatic or aromatic polyurethane, polyurea/urethane or polyurea copolymer comprising, alone or as a mixture, at least one block chosen from:
- a block of aliphatic and/or cycloaliphatic and/or aromatic polyester origin, and/or
- a branched or unbranched silicone block, for example polydimethylsiloxane or polymethylphenylsiloxane, and/or
- a block comprising fluoro groups.

The film-forming polyurethanes as defined in the invention may also be obtained from branched or unbranched polyesters or from alkyds comprising mobile hydrogens, which are modified by reaction with a diisocyanate and a difunctional organic compound (for example dihydro, diamino or hydroxyamino), also comprising either a carboxylic acid or carboxylate group, or a sulfonic acid or sulfonate group, or alternatively a neutralizable tertiary amine group or a quaternary ammonium group.

Among the film-forming polycondensates, mention may also be made of polyesters, polyesteramides, fatty-chain polyesters, polyamides and epoxyester resins.

The polyesters may be obtained, in a known manner, by polycondensation of dicarboxylic acids with polyols, in particular diols.

The dicarboxylic acid may be aliphatic, alicyclic or aromatic. Examples of such acids that may be mentioned include: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norboranedicarboxylic acid, diglycolic acid, thiodipropionic acid, 2,5-naphthalenedicarboxylic acid and 2,6-naphthalenedicarboxylic acid. These dicarboxylic acid monomers may be used alone or as a combination of at least two dicarboxylic acid monomers. Among these monomers, the ones chosen in particular are phthalic acid, isophthalic acid and terephthalic acid.

The diol may be chosen from aliphatic, alicyclic and aromatic diols. The diol used is chosen in particular from: ethylene glycol, diethylene glycol, triethylene glycol, 1,3-propanediol, cyclohexanedimethanol and 4-butanediol. Other polyols that may be used are glycerol, pentaerythritol, sorbitol and trimethylolpropane.

The polyesteramides may be obtained in a manner analogous to that of the polyesters, by polycondensation of diacids with diamines or amino alcohols. Diamines that may be used are ethylenediamine, hexamethylenediamine and meta- or para-phenylenediamine. An amino alcohol that may be used is monoethanolamine.

Polymer of Natural Origin

Use may be made in the present invention of optionally modified polymers of natural origin, such as shellac resin, sandarac gum, dammar resins, elemi gums, copal resins, water-insoluble cellulose-based polymers such as nitrocellulose, modified cellulose esters in particular including carboxyalkyl cellulose esters such as those described in patent application US 2003/185 774, and mixtures thereof.

According to a particular embodiment of the invention, said at least one film-forming polymer in the dispersed state is chosen from acrylic polymer dispersions, polyurethane dispersions, sulfopolyester dispersions, vinyl dispersions, polyvinyl acetate dispersions, vinylpyrrolidone, dimethylaminopropylmethacrylamide and lauryldimethylpropylmethacrylamidoammonium chloride terpolymer dispersions, dispersions of polyurethane/polyacrylic hybrid polymers and dispersions of particles of core-shell type, and mixtures thereof.

Various types of aqueous dispersion, in particular commercial aqueous dispersions, which are suited to the preparation of the composition in accordance with the present invention are detailed below.

1/ Thus, according to one preferred embodiment of the invention, the aqueous dispersion of polymer particles is an aqueous dispersion of acrylic polymer.

The acrylic polymer can be a styrene/acrylate copolymer and in particular a polymer chosen from copolymers resulting from the polymerization of at least one styrene monomer and at least one $C_1$-$C_{18}$ alkyl (meth)acrylate monomer.

As styrene monomer that may be used in the invention, examples that may be mentioned include styrene and α-methylstyrene, and in particular styrene.

The $C_1$-$C_{18}$ alkyl (meth)acrylate monomer is in particular a $C_1$-$C_{12}$ alkyl (meth)acrylate and more particularly a $C_1$-$C_{10}$ alkyl (meth)acrylate. The $C_1$-$C_{18}$ alkyl (meth)acrylate monomer may be chosen from methyl acrylate, methyl methacrylate, ethyl acrylate, propyl acrylate, butyl acrylate, butyl methacrylate, hexyl acrylate, octyl acrylate, 2-ethylhexyl acrylate, lauryl (meth)acrylate and stearyl (meth)acrylate.

As acrylic polymer in aqueous dispersion, use may be made according to the invention of the styrene/acrylate copolymer sold under the name Joncryl SCX-8211® by the company BASF or Syntran 5760CG by the company Interpolymer, the acrylic polymer sold under the reference Acronal® DS-6250 by the company BASF, or the acrylic copolymer Joncryl® 95 by the company BASF.

2/ According to one embodiment variant of the invention, the aqueous dispersion of polymer particles is an aqueous dispersion of polyester-polyurethane and/or polyether-polyurethane particles, in particular in anionic form.

The anionic nature of the polyester-polyurethanes and of the polyether-polyurethanes used according to the invention is due to the presence in their constituent units of groups bearing a carboxylic acid or sulfonic acid function.

The polyester-polyurethane or polyether-polyurethane particles used according to the invention are generally sold in aqueous dispersion form.

The particle content of said dispersions currently available on the market ranges from approximately 20% to approximately 60% by weight relative to the total weight of the dispersion.

Among the anionic polyester-polyurethane dispersions that may be used in the compositions according to the invention, mention may be made in particular of the product sold under the name Avalure UR 405® by the company Noveon or Baycusan C1004 by the company Bayer Material Science.

Among the anionic polyether-polyurethane particle dispersions that may be used according to the invention, mention may be made in particular of the products sold under the name Avalure UR 450® by the company Noveon and under the name Neorez R 970® by the company DSM.

According to a particular embodiment of the invention, use may be made of a mixture of commercial dispersions consisting of anionic polyester-polyurethane particles as defined above and of anionic polyether-polyurethane particles also defined above.

For example, use may be made of a mixture consisting of the dispersion sold under the name Sancure 861® or a mixture of the product sold under the name Avalure UR 405® and of the product sold under the name Avalure UR 450®, these dispersions being sold by the company Noveon.

3/ According to another particular embodiment of the invention, the aqueous dispersion used comprises a mixture of at least two film-forming polymers in the form of particles that differ by their respective glass transition temperatures (Tg).

In particular, according to one embodiment of the invention, the composition in accordance with the invention may comprise at least one first film-forming polymer in the dispersed state and at least one second film-forming polymer in the dispersed state, said first and second polymers having different Tg values and, preferably, the Tg of the first polymer (Tg1) is higher than the Tg of the second polymer (Tg2). In particular, the difference between the Tg1 and Tg2 values is, as an absolute value, at least 10° C. and preferably at least 20° C.

More precisely, it comprises in an acceptable aqueous medium:

a) particles dispersed in the aqueous medium of a first film-forming polymer having at least one glass transition temperature Tg1 greater than or equal to 20° C., and b) particles dispersed in the aqueous medium of a second film-forming polymer having at least one glass transition temperature Tg1 less than or equal to 70° C.

This dispersion generally results from a mixing of two aqueous dispersions of film-forming polymer.

The first film-forming polymer has at least one, and in particular has one, glass transition temperature Tg1 greater than or equal to 20° C., in particular ranging from 20° C. to 150° C. and advantageously greater than or equal to 40° C., in particular ranging from 40° C. to 150° C. and in particular greater than or equal to 50° C., in particular ranging from 50° C. to 150° C.

The second film-forming polymer has at least one, and in particular has one, glass transition temperature Tg2 less than or equal to 70° C., in particular ranging from −120° C. to 70° C., in particular less than 50° C., in particular ranging from −60° C. to +50° C. and more particularly ranging from −30° C. to 30° C.

The measurement of the glass transition temperature (Tg) of a polymer is performed by DMTA (dynamic and mechanical temperature analysis) as described below.

To measure the glass transition temperature (Tg) of a polymer, viscoelasticity tests are performed with a "Polymer Laboratories" DMTA machine, on a sample of film. This film is prepared by pouring the aqueous dispersion of film-forming polymer in a Teflon-coated matrix followed by drying at 120° C. for 24 hours. A film is then obtained, from which specimens are cut out (for example using a punch). These specimens are typically about 150 μm thick, from 5 to 10 mm wide and have a useful length of about 10 to 15 mm. A tensile stress is imposed on this sample. The sample undergoes a static force of 0.01 N on which is superimposed a sinusoidal displacement of ±8 μm at a frequency of 1 Hz. The test is thus performed in the linear range, at low levels of deformation. This tensile stress is performed on the sample at temperatures ranging from −150° C. to +200° C., with a temperature variation of 3° C. per minute.

The complex modulus $E^*=E'+iE''$ of the polymer tested is thus measured as a function of the temperature.

From these measurements, the dynamic moduli E' and E'' and the damping power: tgδ=E''/E' are deduced.

The curve of the tgδ values is then plotted as a function of the temperature; this curve presents at least one peak. The glass transition temperature Tg of the polymer corresponds to the temperature at the top of this peak.

When the curve presents at least two peaks (in this case, the polymer presents at least two Tg values), the value taken as the Tg of the polymer tested is the temperature for which the curve presents a peak of the largest amplitude (i.e. corresponding to the largest tgδ value; in this case, only the "major" Tg is considered as the Tg value of the polymer tested).

In the present invention, the transition temperature Tg1 corresponds to the "major" resents Tg (in the predefined sense) of the first film-forming polymer when the latter presents at least two Tg values; the glass transition temperature Tg2 corresponds to the "major" presents Tg of the second film-forming polymer when the latter presents at least two Tg values.

The first film-forming polymer and the second film-forming polymer may be chosen, independently of each other, from free-radical polymers, polycondensates and polymers of natural origin as defined previously having the glass transition temperature characteristics defined previously.

As first film-forming polymer in aqueous dispersion, use may be made of the aqueous polymer dispersions sold under the names Neorez R-989® by the company DSM, Joncryl 95 and Joncryl® 8211 by the company BASF.

As second film-forming polymer in aqueous dispersion, use may be made, for example, of the aqueous polymer dispersions sold under the names Avalure® UR-405, Avalure® UR-460 by the company Noveon or Acrilem IC89RT® by the company ICAP, and Neocryl A-45 by the company DSM.

The film-forming polymer of the aqueous dispersion Avalure® UR-460 is a polyurethane obtained by polycondensation of polytetramethylene oxide, tetramethylxylylene diisocyanate, isophorone diisocyanate and dimethylolpropionic acid.

According to a most particularly preferred embodiment of the invention, use is made, as first and second film-forming polymers in aqueous dispersion, of the combination of styrene/acrylate polymer dispersion such as the dispersion sold under the reference Joncryl 8211® by BASF and of acrylic polymer dispersion such as the dispersion sold under the reference Neocryl A-45® by DSM.

According to another preferred embodiment of this particular embodiment of point 3/ above of the invention, use is made, as first film-forming polymer in aqueous dispersion, of an acrylic polymer dispersion such as the dispersion sold under the reference Joncryl 95® by BASF and, as second film-forming polymer, of a dispersion of anionic polyurethane polymer sold under the reference Avalure UR405® by DSM.

As aqueous dispersions of film-forming polymer, use may be made of:

the acrylic dispersions sold under the names Acronal DS-6250® by the company BASF, Neocryl A-45®, Neocryl XK-90®, Neocryl A-1070®, Neocryl A-1090®, Neocryl BT-62®, Neocryl A-1079® and Neocryl A-523® by the company DSM, Joncryl 95® and Joncryl 8211® by the company BASF, Daitosol 5000 AD® or Daitosol 5000 SJ by the company Daito Kasey Kogyo; Syntran 5760 CG by the company Interpolymer, the aqueous polyurethane dispersions sold under the names Neorez R-981® and Neorez R-974® by the company DSM, Avalure UR-405®, Avalure LIR-410®, Avalure UR-425®, Avalure UR-450®, Sancure 875®, Avalure UR 445® and Avalure UR 450® by the company Noveon, Impranil 85® by the company Bayer, and Baycusan C1004® by the company Bayer Material Science, the sulfopolyesters sold under the brand name Eastman AQ® by the company Eastman Chemical Products, vinyl dispersions such as Mexomer PAM, aqueous dispersions of polyvinyl acetate such as Vinybran® from the company Nisshin Chemical or the products sold by the company Union Carbide, aqueous dispersions of vinylpyrrolidone, dimethylaminopropylmethacrylamide and lauryldimethylpropylmethacrylamidoammonium chloride terpolymer such as Styleze W® from ISP, aqueous dispersions of polyurethane/polyacrylic hybrid polymer such as the products sold under the references Hybridur® by the company Air Products or Duromer® from National Starch, dispersions of particles of core-shell type such as the products sold by the company Arkema under the reference Kynar® (core: fluorinated—shell: acrylic) or alternatively those described in U.S. Pat. No. 5,188,899 (core: silica—shell: silicone), and mixtures thereof.

According to a preferred embodiment, a composition in accordance with the invention comprises an aqueous dispersion of particles chosen from aqueous dispersions of acrylic film-forming polymer(s) and derivatives, in particular of styrene-acrylic film-forming polymer(s) and derivatives, and aqueous dispersions of polyurethane polymer(s), in particular of polyester-polyurethane polymer(s), and derivatives thereof, and a mixture or mixtures thereof.

Water-Soluble Film-Forming Polymer

The compositions according to the present invention comprise at least one water-soluble film-forming polymer.

Preferably, a composition according to the invention is free of water-soluble film-forming polymer. However, the total solids content of "water-soluble film-forming polymer(s)" may range from 0.1% to 10%, preferably from 0.5% to 8% and better still from 1% to 5% by weight relative to the total weight of the composition.

Examples of water-soluble film-forming polymers that may be mentioned include:

proteins, for instance proteins of plant origin, such as wheat proteins, soya proteins; proteins of animal origin such as keratins, for example keratin hydrolysates and sulfonic keratins;

cellulose polymers such as hydroxyethyl cellulose, hydroxypropyl cellulose, methyl cellulose, ethyl hydroxyethyl cellulose and carboxymethyl cellulose, and also quaternized cellulose derivatives;

acrylic polymers or copolymers, such as polyacrylates or polymethacrylates;

vinyl polymers, such as polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;

anionic, cationic, amphoteric or nonionic chitin or chitosan polymers;

gum arabic, guar gum, xanthan derivatives, karaya gum, acacia gum;

alginates and carrageenans;

glycoaminoglycans, hyaluronic acid and its derivatives;

deoxyribonucleic acid;

mucopolysaccharides such as chondroitin sulfates;

and mixtures thereof.

Gelling Agents

Hydrophilic Gelling Agents

The compositions according to the present invention may also contain at least one hydrophilic, or water-soluble, gelling agent, which may be chosen from:

acrylic or methacrylic acid homopolymers or copolymers or the salts thereof and esters thereof and in particular the products sold under the names Versicol F® or Versicol K® by the company Allied Colloid, Ultrahold 8® by the company Ciba-Geigy, and polyacrylic acids of Synthalen K type, copolymers of acrylic acid and of acrylamide sold in the form of the sodium salt thereof under the names Reten® by the company Hercules, and the sodium salts of polyhydroxycarboxylic acids sold under the name Hydagen F® by the company Henkel, polyacrylic acid/alkyl acrylate copolymers of Pemulen type;

AMPS (polyacrylamidomethylpropanesulfonic acid partially neutralized with aqueous ammonia and highly crosslinked) sold by the company Clariant, AMPS/acrylamide copolymers of Sepigel® or Simulgel® type sold by the company SEPPIC, and AMPS/polyoxyethylenated alkyl methacrylate copolymers (crosslinked or non-crosslinked), and mixtures thereof.

associative polymers and in particular associative polyurethanes such as the $C_{16}$-$OE_{120}$-$C_{16}$ polymer from the company Elementis (sold under the name Rheolate FX1100, this molecule bearing a urethane function and having a weight-average molecular weight of 1300), OE being an oxyethylene unit, Rheolate 205 bearing a urea function, sold by the company Rheox, or also Rheolate 208 or 204 (these polymers being sold in pure form) or DW 1206B from Röhm & Haas bearing a $C_{20}$ alkyl chain and a urethane bond, sold at 20% solids in water. It is also possible to use solutions or dispersions of these associative polyurethanes, in particular in water or in aqueous-alcoholic medium. Examples of such polymers that may be mentioned include Rheolate FX1010, Rheolate FX1035, Rheolate1070, Rheolate 255, Rheolate 278 and Rheolate 244 sold by the company Elementis. It is also possible to use the products DW 1206F and DW 1206J, and also Acrysol RM 184 or Acrysol 44 from the company Röhm & Haas, or alternatively Borchigel LW 44 from the company Borchers, and mixtures thereof.

Some water-soluble film-forming polymers also act as water-soluble gelling agent.

The hydrophilic gelling agents may be present in the compositions according to the invention in a content ranging from 0.05% to 10% by weight, preferably from 0.1% to 5% by weight and better still from 0.5% to 2% by weight, relative to the total weight of the composition.

A composition according to the invention advantageously comprises one of the abovementioned gelling agents, preferably chosen from AMPS (polyacrylamidomethylpropanesulfonic acid partially neutralized with ammonia and highly crosslinked), AMPS/acrylamide copolymers, and a mixture thereof.

Lipophilic Gelling Agents

A composition according to the invention may comprise at least one lipophilic or liposoluble gelling agent.

The gelling agent(s) that may be used may be organic or mineral, polymeric or molecular lipophilic gelling agents.

Mineral lipophilic gelling agents that may be mentioned include clays, modified clays, such as Bentone 38 VCG by the company Elementis, and optionally hydrophobically surface-treated fumed silica.

The polymeric organic lipophilic gelling agents are, for example, partially or completely crosslinked elastomeric organopolysiloxanes of three-dimensional structure, such as the products sold under the names KSG6®, KSG16® and KSG18® by the company Shin-Etsu, TREFIL E-505C® and Trefil E-506C® by the company Dow Corning, Gransil SR-CYC®, SR DMF10®, SR-DC556®, SR 5CYC Gel®, SR DMF 10 Gel® and SR DC 556 Gel® by the company Grant Industries and SF 1204® and JK 113® by the company General Electric; ethyl cellulose, such as the product sold under the name Ethocel® the company by Dow Chemical; polycondensates of polyamide type resulting from the condensation between (α) at least one acid chosen from dicarboxylic acids containing at least 32 carbon atoms, such as fatty acid dimers, and (β) an alkylenediamine and in particular ethylenediamine, in which the polyamide polymer comprises at least one carboxylic acid end group esterified or arnidated with at least one saturated and linear monoalcohol or monoamine containing from 12 to 30 carbon atoms, and in particular ethylenediamine/stearyl dilinoleate copolymers such as the product sold under the name Uniclear 100 VG® by the company Arizona Chemical; silicone polyamides of the polyorganosiloxane type such as those described in U.S. Pat. Nos. 5,874,069, 5,919,441, 6,051,216 and 5,981,680, for instance the products sold under the references Dow Corning 2-8179 and Dow Corning 2-8178 Gellant by the company Dow Corning. Block copolymers of "diblock", "triblock" or "radial" type, of the polystyrene/polyisoprene or polystyrene/polybutadiene type, such as the products sold under the name Luvitol HSB® by the company BASF, of the polystyrene/copoly(ethylene-propylene) type, such as the products sold under the name Kraton® by the company Shell Chemical Co., or also of the polystyrene/copoly(ethylene-butylene) type, and mixtures of triblock and radial (star) copolymers in isododecane, such as the products sold by the company Penreco under the name Versagel®, for instance the mixture of butylene/ethylene/styrene triblock copolymer and of ethylene/propylene/styrene star copolymer in isododecane (Versagel M 5960).

The compositions according to the invention may also comprise a non-emulsifying silicone elastomer as lipophilic gelling agent. Among the lipophilic gelling agents that may also be mentioned are organogelling agents.

A composition according to the invention is preferably free of lipophilic gelling agent.

Cosmetic Active Agents

The compositions in accordance with the invention may also comprise at least one cosmetic active agent.

As cosmetic active agents that may be used in the compositions in accordance with the invention, mention may be made in particular of antioxidants, preserving agents, fragrances, neutralizers, emollients, coalescers, moisturizers, vitamins and screening agents, in particular sunscreens, and mixtures thereof.

Needless to say, those skilled in the art will take care to select the optional additional ingredients and/or the amount thereof such that the advantageous properties of the composition according to the invention are not, or are not substantially, adversely affected by the envisaged addition.

Preferably, the composition according to the invention is a leave-in composition. Advantageously, the composition is a makeup composition and in particular a mascara.

Oil or Organic Solvent

The compositions according to the invention may comprise at least one oil or organic solvent.

The compositions according to the invention may in particular comprise at least one oil chosen from at least one non-volatile oil, at least one volatile oil, and a mixture thereof.

Non-Volatile Oil

The term "oil" means a fatty substance that is liquid at ambient temperature and at atmospheric pressure.

The term "non-volatile oil" means an oil that remains on the skin or the keratin fibre at ambient temperature and pressure. More precisely, a non-volatile oil has an evaporation rate strictly less than 0.01 mg/cm$^2$/min.

To measure this evaporation rate, 15 g of oil or of oil mixture to be tested are placed in a crystallizing dish 7 cm in diameter, which is placed on a balance in a large chamber of about 0.3 m$^3$ that is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing said oil or said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit of area (cm$^2$) and per unit of time (minutes).

Said at least one non-volatile oil may be chosen from hydrocarbon-based oils and silicone oils, and mixtures thereof, preferably from hydrocarbon-based oils.

The non-volatile hydrocarbon-based oils that are suitable for the present invention may be chosen in particular from:
 hydrocarbon-based oils of plant origin, such as triglycerides consisting of fatty acid esters of glycerol, the fatty acids of which may have chain lengths ranging from C4 to C28, these fatty acids possibly being linear or branched, and saturated or unsaturated; these oils are in particular wheatgerm oil, sunflower oil, grapeseed oil, sesame oil, corn oil, apricot oil, castor oil, shea oil, avocado oil, olive oil, soybean oil, sweet almond oil, rapeseed oil, cottonseed oil, hazelnut oil, macadamia oil, jojoba oil, palm oil, alfalfa oil, poppy oil, pumpkin oil, marrow oil, blackcurrant oil, evening primrose oil, millet oil, barley oil, quinoa oil, rye oil, safflower oil, candlenut oil, passion flower oil and musk rose oil; or alternatively caprylic/capric acid triglycerides such as those sold by the company Stéarineries Dubois or those sold under the names Miglyol 810®, 812® and 818® by the company Sasol;
 synthetic ethers containing from 10 to 40 carbon atoms;
 linear or branched hydrocarbons of mineral or synthetic origin other than the polymers according to the invention, such as petroleum jelly, polybutenes, polydecenes and squalane, and mixtures thereof;
 synthetic esters such as the oils of formula R1COOR2 in which R1 represents the linear or branched fatty acid residue containing from 1 to 40 carbon atoms and R2 represents an in particular branched hydrocarbon-based chain containing from 1 to 40 carbon atoms, on condition that R1+R2≥10, for instance purcellin oil (cetostearyl octanoate), isopropyl myristate, isopropyl palmitate, C12 to C15 alkyl benzoate, hexyl laurate, diisopropyl adipate, isononyl isononanoate, 2-ethylhexyl palmitate, isostearyl isostearate, alkyl or polyalkyl octanoates, decanoates or ricinoleates such as propylene glycol dioctanoate; hydroxylated esters such as isostearate lactate and diisostearyl malate; and pentaerythritol esters;
 fatty alcohols that are liquid at ambient temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol; and
 higher fatty acids such as oleic acid, linoleic acid or linolenic acid, and mixtures thereof.

The non-volatile silicone oils that are suitable for the present invention may be chosen in particular from:
 the non-volatile silicone oils that may be used in the composition in accordance with the invention may be non-volatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, such as phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

A composition according to the invention optionally comprises at least one non-volatile hydrocarbon-based oil of plant origin, such as triglycerides consisting of fatty acid esters of glycerol the fatty acids of which may have chain lengths ranging from C4 to C28, in particular palm oil and hydrogenated jojoba oil. A composition according to the invention is preferably free of silicone non-volatile oil(s).

A composition according to the invention is preferably free of non-volatile oil. However, the total content of non-volatile oil(s) in a composition in accordance with the invention may range from 0.01% to 10% by weight, in particular from 0.1% to 8% by weight and preferably from 0.25% to 5% by weight relative to the total weight of the composition.

According to one preferred embodiment, a composition according to the invention comprises less than 5% by weight of non-volatile oil(s) relative to the total weight of the composition.

Volatile Oil

The composition according to the invention may comprise at least one volatile oil.

The term "volatile oil" means an oil (or non-aqueous medium) that can evaporate on contact with the skin in less than one hour, at ambient temperature and atmospheric pressure. The volatile oil is a cosmetic volatile oil, which is liquid at ambient temperature. More specifically, a volatile oil has an evaporation rate of between 0.01 and 200 mg/cm$^2$/min, limits included.

This volatile oil may be hydrocarbon-based.

The volatile hydrocarbon-based oil may be chosen from hydrocarbon-based oils containing from 7 to 16 carbon atoms.

The composition according to the invention may contain one or more volatile branched alkanes. The expression "one or more volatile branched alkanes" means, without preference, "one or more volatile branched alkane oils".

As a volatile hydrocarbon-based oil containing from 7 to 16 carbon atoms, mention may be made in particular of C8-C16 branched alkanes, such as C8-C16 isoalkanes (also known as isoparaffins), isododecane, isodecane, isohexadecane and for example the oils sold under the trade names Isopar or Permethyl, C8-C16 branched esters such as isohexyl neopentanoate, and mixtures thereof. Preferably, the volatile hydrocarbon-based oil containing from 8 to 16 carbon atoms is chosen from isododecane, isodecane and isohexadecane, and mixtures thereof, and is in particular isododecane.

The composition according to the invention may contain one or more volatile linear alkanes. The term "one or more volatile linear alkanes" means, without preference, "one or more volatile linear alkane oils".

A volatile linear alkane that is suitable for the invention is liquid at ambient temperature (about 25° C.) and at atmospheric pressure (760 mmHg).

A "volatile linear alkane" that is suitable for the invention means a cosmetic linear alkane, which is capable of evaporating on contact with the skin in less than one hour, at ambient temperature (25° C.) and atmospheric pressure (760 mmHg, i.e. 101 325 Pa), which is liquid at ambient temperature, in particular having an evaporation rate ranging from 0.01 to 15 mg/cm$^2$/min, at ambient temperature (25° C.) and atmospheric pressure (760 mmHg).

The linear alkanes, preferably of plant origin, comprise from 7 to 15 carbon atoms, in particular from 9 to 14 carbon atoms and more particularly from 11 to 13 carbon atoms. As examples of linear alkanes that are suitable for the invention, mention may be made of the alkanes described in patent applications WO 2007/068 371 or WO 2008/155 059 by the company Cognis (mixtures of distinct alkanes that differ by at least one carbon). These alkanes are obtained from fatty alcohols, which are themselves obtained from coconut oil or palm oil.

As examples of linear alkanes that are suitable for the invention, mention may be made of n-heptane (C7), n-octane (C8), n-nonane (C9), n-decane (C10), n-undecane (C11), n-dodecane (C12), n-tridecane (C13), n-tetradecane (C14) and n-pentadecane (C15), and mixtures thereof, and in particular the mixture of n-undecane (C11) and n-tridecane (C13) described in Example 1 of patent application WO 2008/155 059 by the company Cognis. Mention may also be made of n-dodecane (C12) and n-tetradecane (C14) sold by Sasol under the references, respectively, Parafol 12-97 and Parafol 14-97, and also mixtures thereof.

The linear alkane may be used alone or as a mixture of at least two distinct alkanes that differ from each other by a carbon number of at least 1, and in particular a mixture of at least two linear alkanes comprising from 10 to 14 distinct carbon atoms that differ from each other by a carbon number of at least 2, and in particular a mixture of C11/C13 volatile linear alkanes or a mixture of C12/C14 linear alkanes, in particular an n-undecane/n-tridecane mixture (such a mixture may be obtained according to Example 1 or Example 2 of WO 2008/155 059).

As a variant or additionally, the composition prepared may comprise at least one volatile silicone oil or solvent that is compatible with cosmetic use.

The term "silicone oil" means an oil containing at least one silicon atom, and in particular containing Si—O groups. According to one embodiment, said composition comprises less than 10% by weight of non-volatile silicone oil(s), relative to the total weight of the composition, better still less than 5% by weight, or even is free of silicone oil.

Volatile silicone oils that may be mentioned include cyclic polysiloxanes and linear polysiloxanes, and mixtures thereof. Volatile linear polysiloxanes that may be mentioned include hexamethyldisiloxane, octamethyltrisiloxane, decamethyltetrasiloxane, tetradecamethylhexasiloxane and hexadecamethylheptasiloxane. Volatile cyclic polysiloxanes that may be mentioned include hexamethylcyclotrisiloxane, octamethylcyclotetrasiloxane, decamethylcyclopentasiloxane and dodecamethylcyclohexasiloxane.

As a variant or additionally, the composition prepared may comprise at least one volatile fluoro oil.

The term "fluoro oil" means an oil containing at least one fluorine atom.

Volatile fluoro oils that may be mentioned include nonafluoromethoxybutane and perfluoromethylcyclopentane, and mixtures thereof.

A composition according to the invention is preferably free of non-volatile oil. However, at least one volatile oil may be present in a total content ranging from 0.1% to 10% by weight. In particular, the volatile oil may be present in the composition in a content ranging from 0.5% to 5% by weight relative to the total weight of the composition.

According to one preferred embodiment, a composition according to the invention comprises less than 5% by weight of volatile oil(s) relative to the total weight of the composition.

Assembly

An assembly for coating keratin fibres suitable for the invention may comprise an applicator suitable for applying said cosmetic composition for coating keratin fibres and, where appropriate, a packaging device suitable for receiving said composition.

Applicator

The applicator may comprise means for smoothing and/or separating keratin fibres, such as the eyelashes or the eyebrows, in particular in the form of teeth, bristles or other reliefs.

The applicator is arranged to apply the composition to the eyelashes or the eyebrows, and may comprise, for example, a brush or a comb.

The applicator may also be used for finishing of the makeup, over a region of the eyelashes or eyebrows that is made up or laden with composition.

The brush may comprise a twisted core and bristles held between the turns of the core, or may be made in yet another way.

The comb is, for example, produced from a single part by moulding of a plastic.

In certain exemplary embodiments, the application member is mounted at the end of a wand, which wand may be flexible, which may contribute to improving the comfort during application.

Packaging Device

The packaging device may comprise a container for housing the composition for coating keratin fibres. This composition may then be withdrawn from the container by immersing the applicator therein.

This applicator may be firmly attached to a member for closing the container. This closing member may form a member for gripping the applicator. This gripping member may form a cap to be removably mounted on said container by any suitable means, such as screwing, click-fastening, coupling, etc. Such a container may thus reversibly house said applicator.

This container may be optionally equipped with a wiper suitable for removing surplus product taken up by the applicator.

A process for applying the composition according to the invention to the eyelashes or the eyebrows may also include the following steps:

forming a deposit of the cosmetic composition on the eyelashes or the eyebrows,
  leaving the deposit on the eyelashes or the eyebrows, it being possible for the deposit to dry.

It should be noted that, according to another embodiment, the applicator may form a product container. In such a case, a container may, for example, be provided in the gripping member and an internal channel can internally connect this gripping member to the application members in relief.

Finally, it should be noted that the packaging and application assembly may be in the form of a kit, it being possible for the applicator and the packaging device to be housed separately in the same packaging article.

The examples above and that follow are given as illustrations of the present invention, and shall not limit the scope thereof.

EXAMPLES

A mascara composition in accordance with the invention is described below and compared to two compositions outside the invention:

| Ingredients with percentage contents | Composition A according to the invention | Comparative composition 1 outside the invention | Comparative composition 2 outside the invention |
|---|---|---|---|
| Steareth 2 (Brij 72 from Uniqema) | 12.2 | 4 | 10 |
| Steareth 20 (Brij 78P from Uniqema) | 12.2 | 4 | 3 |
| Powder of hexamethylene/trimethylol hexyl lactone copolymer containing silica (Plastic Powder D 400) | 12.2 | 12.2 | 12.2 |
| Pigments (iron oxides) | 12.2 | 12.2 | 12.2 |
| Water | qs 100 | qs 100 | qs 100 |
| Preserving agents | qs | qs | qs |

These compositions were prepared as follows:

The ingredients are weighed out, the Steareth 2 and 20 in accordance with the invention are melted at 80° C., and the water preheated in an electric kettle to 95° C. and the pigments are then added. Mixing is carried out for 5 minutes at 95° C. using a Moritz blender.

The preservatives are poured into the mixture when the temperature of the mixture is less than or equal to 45° C.

The mascara thus obtained is transferred into a closed jar to prevent it from drying out on contact with air; it is then necessary to wait 24 hours to check the homogeneity of the formulation and the correct dispersion of the pigments.

1/Verification of the Presence of a Lamellar Phase Lβ

The presence of a lamellar phase Lβ was first of all suspected by means of an optical microscope with cross-polarized light with a magnification of 10.

It should be noted that the characterization of a lamellar phase Lβ using the technique of wide angle X-ray scattering previously explained should be carried out essentially on a combination of surfactant system and aqueous phase in order to avoid any scattering which might mask the lamellar-phase lines, capable of disrupting the measurements. Thus, this measurement should be carried out on a composition free of pigments and of fillers. This measurement was carried out on the following composition:

| Ingredients with percentage contents | Composition A' according to the invention | Comparative composition 2' outside the invention |
|---|---|---|
| STEARETH 2 (Brij 72 from Uniqema) | 7 | 10 |
| STEARETH 20 (Brij 78P from Uniqema) | 15 | 3 |
| Water | qs 100 | qs 100 |
| Preserving agents | qs | qs |

The x-ray diffraction spectrum of this composition A' according to the invention shows three fine lines at q equal to 0.052, q equal to 0.107 and q equal to 0.16 $\text{angstrom}_{-1}$, which gives us a period for the lamellar phase of 120 angstroms.

It should be noted that, although the surfactant contents were slightly modified compared with the example of composition A according to the invention previously given, a similar, or even identical, X-ray diffraction spectrum would be obtained with the surfactant contents of said composition A free of pigments and of fillers.

As regards comparative composition 2' outside the invention, the presence of 13% by weight of a mixture of surfactants with an HLB at 25° C. of less than 8 and with an HLB at 25° C. of greater than or equal to 8 does not make it possible to form an Lβ lamellar phase.

2/ Protocols and Results

The composition A prepared is observed with the naked eye and under a microscope, and then tested on a test sample of bare eyelashes, by application of these compositions using a brush.

The composition A according to the invention exhibits, to the naked eye and under a microscope, a fine dispersion of particles (pigments and spherical fillers). This composition exhibits a black colour of good intensity.

The composition in accordance with the invention is pleasant to apply, it has a fluid texture (viscosity at 25° C. of 7.1 Pa·s measured with the Rheomat RM100® machine), the deposit is constructed coat after coat, the composition coats the eyelashes well, the makeup result is uniform and the eyelash fringe is well spread out. In addition, the composition obtained has good sheen.

In addition, these compositions are stable at 4 and 45° C. for two months.

The compositions outside the invention are too fluid and do not make it possible to obtain the qualities of composition A.

Other Examples of Surfactant Systems According to the Invention

Other compositions according to the invention using variants of the surfactant system in accordance with the invention were prepared and the presence of a lamellar phase was checked with a cross-polarized light microscope, with a magnification of 10.

Composition B (According to the Invention):

| Ingredients with percentage contents | Composition B according to the invention |
|---|---|
| Sucrose tristearate (Ryoto Sugar Ester S 370 from Mitsubishi-Kagaku Foods) | 10 |
| Polysorbate 60 (Tween 60-SS-(TH) from Croda) | 10 |
| Water | qs 100 |

Composition C (According to the Invention):

| Ingredients with percentage contents | Composition C according to the invention |
|---|---|
| Steareth 2 (Brij S2-SO-(TH) from Croda) | 10 |
| PEG-40 stearate (Myrj S40-FL-(TH) from Croda) | 10 |
| Water | qs 100 |

Composition D (According to the Invention):

| Ingredients with percentage contents | Composition D according to the invention |
|---|---|
| Glyceryl stearate (Tegin 90 Pellets from Evonik Goldschmidt) | 10 |
| PEG-40 stearate/(Myrj S40-FL-(TH) from Croda) | 10 |
| Water | qs 100 |

Composition E (According to the Invention):

| Ingredients with percentage contents | Composition E according to the invention |
|---|---|
| Steareth 2 (Brij S2-SO-(TH) from Croda) | 10 |
| PEG-200 glyceryl stearate (Simulsol 220 TM from SEPPIC) | 10 |
| Water | qs 100 |

Results

For compositions 2B to 2E according to the invention, the formation of a lamellar phase Lβ was observed for each (presence of Maltese crosses, birefringent structures and oily striations).

Example of a Surfactant System Outside the Invention

| Ingredients with percentage contents | Comparative composition 3 outside the invention |
|---|---|
| Steareth 2 (Brij S2-SO-(TH) from Croda) | 10 |
| Cetyl phosphate (Amphisol K from DSM Nutritional Products) | 10 |
| Water | qs 100 |

Such a surfactant system does not allow the formation of a lamellar phase Lβ.

It is understood that, in the context of the present invention, the weight percentages given for a compound or a family of compounds are always expressed as weight of solids of the compound in question.

Throughout the application, the wording "comprising one" or "containing one" means "comprising at least one" or "containing at least one", unless otherwise specified.

The invention claimed is:

1. A cosmetic composition for coating keratin fibres, the cosmetic composition comprising:
an aqueous phase present in a content of 30% to 70% by weight relative to a total weight of the cosmetic composition;
a surfactant system;
at least one spherical filler,
wherein the surfactant system comprises
i) a nonionic surfactant with an HLB value at 25° C. of less than 8, and
ii) a nonionic surfactant with an HLB value at 25° C. of greater than or equal to 8,
wherein the nonionic surfactant i) and the nonionic surfactant ii) are present in a total content of greater than or equal to 15% by weight relative to a total weight of the cosmetic composition and together form a lamellar phase Lβ,
wherein a total wax content of the cosmetic composition is 5% or less by weight relative to the total weight of the cosmetic composition, and
wherein the nonionic surfactant i) and the nonionic surfactant ii) are defined by formula (I'):

$$ALK\text{-}(O\text{---}CH_2\text{---}CH_2)_n\text{---}OH \qquad (I'),$$

wherein:
ALK is a $C_8$-$C_{24}$ alkyl group; and
n is an integer between 1 and 200.

2. The composition of claim 1, wherein ALK is a $C_{12}$-$C_{18}$ alkyl group in the nonionic surfactant ii).

3. The composition of claim 1, wherein ALK is a stearyl group in the nonionic surfactant i) and the nonionic surfactant ii).

4. The composition of claim 1, wherein the nonionic surfactant i) is steareth-2 and the nonionic surfactant ii) is steareth-20.

5. The composition of claim 1, wherein the nonanionic surfactant ii) is present in a content of greater than or equal to 5% by weight relative to the total weight of the cosmetic composition.

6. The composition of claim 1, wherein the nonanionic surfactant i) is present in a content of greater than or equal to 5% by weight relative to the total weight of the cosmetic composition.

7. The composition of claim 1, wherein the nonionic surfactant i) and the nonionic surfactant ii) are present in a total content of from 18-30% by weight relative to the total weight of the cosmetic composition.

8. The composition of claim 1, wherein a weight ratio of the nonionic surfactant i) relative to the nonionic surfactant ii) ranges from 1/5 to 5/1.

9. The composition of claim 1, where the at least one spherical filler is selected from the group consisting of a silica powder, a powder of an acrylic (co)polymer, a polyurethane powder, a silicone powder, a polyamide powder and mixtures thereof.

10. The composition of claim 1, wherein the at least one spherical filler is present in a total content of greater than or equal to 5% by weight, relative to the total weight of the cosmetic composition.

11. The composition of claim 1, wherein a wax content of the cosmetic composition is less than 2% by weight relative to the total weight of the cosmetic composition.

12. The composition of claim 1, comprising at least an aqueous dispersion of particles of at least one film-forming polymer.

13. The composition of claim 1, further comprising at least one dye which is a pulverulent substance.

14. The composition of claim 1, having a viscosity at 25° C. ranging from 5 to 50 Pa·s.

15. A process for coating keratin fibres, the process comprising applying the cosmetic composition of claim 1 to keratin fibres.

16. The composition of claim 1, wherein the composition is free of wax.

17. The composition of claim 1, wherein the composition is free of oil and organic solvent.

18. The composition of claim 1, wherein the composition is free of alkyl phosphates and amphoteric surfactants.

19. The composition of claim 1, wherein the at least one spherical filler and the surfactant system are present in a weight ratio range of the at least one spherical filler to the surfactant system of from 1:5 to 6:5.

20. The composition of claim 1, wherein a total solids content of the composition is from 42% by weight or more to less than 60% by weight relative to the total weight of the cosmetic composition.

* * * * *